United States Patent [19]

Tuttle et al.

[11] Patent Number: 5,477,002
[45] Date of Patent: Dec. 19, 1995

[54] ANTHER-SPECIFIC CDNA SEQUENCES, GENOMIC DNA SEQUENCES AND RECUMBINANT DNA SEQUENCES

[75] Inventors: Annmarie B. Tuttle, Garner; Lyle D. Crossland, Chapel Hill, both of N.C.

[73] Assignee: Ciba-Geigy Corporation, Ardsley, N.Y.

[21] Appl. No.: 207,904

[22] Filed: Mar. 7, 1994

Related U.S. Application Data

[63] Continuation of Ser. No. 908,242, Jul. 2, 1992, abandoned.

[51] Int. Cl.$^6$ ............................. A01H 5/00; C12N 15/11; C12N 15/82
[52] U.S. Cl. ................ 800/205; 435/172.3; 435/320.1; 536/23.1; 536/23.5; 536/23.6; 536/23.7; 536/24.1; 935/6; 935/35
[58] Field of Search ............................ 435/172.1, 172.3, 435/320.1; 800/205, DIG. 43; 935/6, 27, 35, 67; 536/23.1, 23.5, 23.6, 24.1, 23.7

[56] References Cited

U.S. PATENT DOCUMENTS 5,086,169  2/1992  Mascarenhas ............................ 536/27

FOREIGN PATENT DOCUMENTS

| 344029 | 4/1989 | European Pat. Off. . |
| 0420819 | 4/1991 | European Pat. Off. . |
| WO89/10396 | 11/1989 | WIPO . |
| WO90/08831 | 8/1990 | WIPO . |
| WO90/08828 | 8/1990 | WIPO . |
| WO90/08825 | 8/1990 | WIPO . |

OTHER PUBLICATIONS

Mariani, C. et al., "Induction of male sterility in plants by a chimaeric ribonuclease gene", *Nature*, 347:737–741 (1990).
Tuttle et al., "Expression of tobacco anther–specific genes", *J. Cell. Biochem.*, Abstract D229, 1993.
J. Kamalay et al (1984) Proc Natl Acad Sci USA 81:2801–2805.

M Bevan et al. (1983) Nucleic Acids Research 11:369–385.
Albani et al., *Plant Molecular Biology*, 15:605–622 (1990).
Guerrero et al., *Mol Gen Genet*, 224:161–168 (1990).
Paul et al., *Plant Molecular Biology*, 19:611–622 (1992).
Mascarenhas, Joseph P., Annu. Rev. Plant Physiol. Plant Mol. Biol. 41:317–338 (1990).
Seurinck et al., *Nucleic Acids Research*, 18(11):3403 (1990).
Huang et al., *PNAS USA*, 88:10716–10720 (1991).
Gearing et al., *EMBO J.*, 5:3651–3655 (1986).
Evard et al., *Plant Mol. Biol.*, 16:271–281 (1991).
Domon et al., *Mol. Gen. Genet.*, 229:238–244 (1991).
Domon et al., *Plant Mol. Biol.* 15:643–646 (1990).
Scott et al., *Plant Mol. Biol.*, 17:195–207 (1991).
Albani et al., *Plant Mol. Biol.*, 16:501–513 (1991).
Albani et al., *Plant Mol. Biol.*, 15:605–622 (1990).
Koltunow et al., *Plant Cell*, 2:1201–1224 (1990).
Twell et al., *Genes and Development*, 5:496–507 (1991).
Wing et al., *Plant Mol. Biol.*, 14:17–28 (1989).
Twell et al., *Mol. Gen. Genet.*, 217:240–245 (1989).
Ursin et al., *Plant Cell*, 1:727–736 (1989).
Smith et al., *Mol. Gen. Genet.*, 229:9–16 (1990).
Gasser et al., *Plant Cell*, 1:15–24 (1989).

(List continued on next page.)

*Primary Examiner*—David T. Fox
*Assistant Examiner*—Bruce R. Campell
*Attorney, Agent, or Firm*—W. Murray Spruill

[57] ABSTRACT cDNA sequences are disclosed which are expressed specifically in the anther of a plant. Genomic DNA sequences corresponding to the cDNA clones are obtained using the cDNA clones as hybridization probes. Recombinant, or chimeric, DNA sequences are constructed in which the promoter sequence from anther-specific genomic clones are operatively linked to a DNA sequence coding for a desired polypeptide. Transgenic plants are made in which the chimeric DNA sequences are expressed in the anther of the transgenic plant. In a preferred embodiment, the coding DNA sequence expresses a polypeptide which will disrupt formation of viable pollen, resulting in a male-sterile plant.

15 Claims, 9 Drawing Sheets

OTHER PUBLICATIONS

McCormick et al., *Tomato Biotechnology*, Alan R. Liss, Inc, 1987, pp. 255–265.

Maeser et al., *Mol. Gen. Genet.*, 230:170–176 (1991).

McCormick, TIG, 7(9) 1991.

Schmitz et al., *Plant Cell*, 1:783–791 (1989).

von Heijne, et al., *Eur. J. Biochem.*, 180:535–545 (1989).

Della–Cioppa et al., *Plant Physiol.*, 84:965–968 (1987).

Schekman, *TIBS*, 177 (1985).

ANTHER-SPECIFIC CDNA SEQUENCES, GENOMIC DNA SEQUENCES AND RECUMBINANT DNA SEQUENCES

This application is a continuation of application Ser. No. 07/908,242, filed Jul. 2, 1992, now abandoned.

FIELD OF THE INVENTION

The present invention relates to novel anther specific cDNA sequences and genomic DNA sequences and recombinant DNA sequences which are expressed specifically in the anther of a plant. The present invention further relates to novel DNA sequences which function as promoters of anther-specific transcription of associated coding DNA sequences in recombinant or chimeric DNA sequences. The chimeric DNA sequences may be used to create male-sterile plants.

BACKGROUND OF THE INVENTION

The creation of male sterile plants is of economic interest in the production of hybrid seeds. Male sterility prevents self-pollination which otherwise occurs in many plant species and hinders breeding and hybrid seed production.

Transcription of many plant genes is controlled in a temporal and spatial manner. Regulation of gene activity is mediated by the interaction of trans acting factors and cis regulatory elements in the promoter region of a gene.

Of particular interest are genes which are expressed primarily or exclusively in the sexual tissue of the plant, such as anther or pollen tissue. Such genes can be used to express polypeptides that are not naturally produced in the anther or pollen. For example, the promoter region from an anther specific gene may be used to express a polypeptide which will disrupt formation of viable pollen when expressed in the anther cells, resulting in a male sterile plant European Patent Application 0 420 819 A1 describes the use of the wun1 gene to produce male sterile plants.

U.S. Pat. No. 5,086,169 describes the isolation of the promoter region from the Zm13 clone of a pollen-specific gene of corn, and its use to express genes in pollen.

PCT WO 89/10396 describes the use of male-sterility DNAs and anther-specific cDNAs TA13, TA26 and TA29. The developmental expression profiles of TA13 and TA29 matched two cDNA clones isolated by the applicants, ANT5 and ANT45, respectively.

PCT WO 90/08825 describes three gene sequences, pMS10, pMS14 and pMS18, and their use in recombinant DNA sequences with the GUS reporter gene GUS. No evidence of expression is given.

PCT WO 90/08831 describes a disrupter gene known as the mammalian uncoupling protein (UCP) gene which inhibits respiration in cells.

PCT WO 90/08828 describes molecular methods of hybrid seed production in which recombinant DNA molecules using pollen specific promoters are used to control the production of fertile pollen in plants.

SUMMARY OF THE INVENTION

It is one object of the present invention to provide anther-specific cDNA clones.

It is another object of the present invention to provide DNA sequences which are expressed specifically in the anther of a plant.

It is another object of the present invention to provide DNA sequences and vectors which direct the anther-specific expression of genes in plants.

According to the present invention, novel DNA sequences are provided which are expressed specifically in the anther of a plant. Several cDNA sequences are provided which may be used as probes to isolate anther-specific genomic DNA sequences. Two genomic DNA sequences are provided which are expressed specifically in the anther of a plant. Anther-specific promoter DNA sequences are isolated from these genomic clones and are ligated to coding DNA sequences to provide chimeric vectors that are specifically expressed in the anther of a plant.

In one embodiment, the present invention comprises an isolated nucleotide sequence consisting essentially of an anther-specific cDNA sequence. The cDNA sequence is obtained by differential screening of cDNA libraries and selecting those cDNA clones which are observed to be expressed in a highly specific manner in anther tissue. The cDNA clones of the present invention may have the DNA sequences of SEQ ID No. 1, SEQ. ID No. 3, SEQ. ID No. 5, SEQ. ID No. 7, SEQ. ID No. 9, SEQ. ID No. 11, SEQ. ID No. 13, SEQ. ID No. 14 and SEQ. ID No. 20.

In another embodiment, the present invention comprises an isolated genomic DNA sequence corresponding to an anther-specific cDNA clone. The genomic DNA sequences of the present invention are obtained by hybridization of a genomic library with the anther-specific cDNA sequence used as a probe. The genomic DNA sequences of the present invention may have the DNA sequences of SEQ. ID No. 16 and SEQ. ID No. 18, or they may be obtained by hybridization with a cDNA having the DNA sequence of SEQ. ID No. 1, SEQ. ID No. 3, SEQ. ID No. 5, SEQ. ID No. 7, SEQ. ID No. 9, SEQ. ID No. 11, SEQ. ID No. 13, SEQ. ID No. 14 and SEQ. ID No. 20.

In yet another embodiment, the present invention comprises isolated recombinant, or chimeric, DNA sequences in which the promoter region from an anther-specific genomic DNA sequence is operatively linked to a DNA sequence which encodes a protein which is desired to be expressed in the anther cells. For example, the isolated recombinant DNA sequences of the present invention may comprise, in a 5' to 3' direction, the promoter region from an anther-specific genomic DNA sequence may be operatively linked to a DNA sequence which encodes a polypeptide which will disrupt formation of viable pollen when expressed in the anther cells. The resulting plant will not be able to produce viable pollen cells, and hence will be male sterile. Examples of such a recombinant DNA sequence include chimeric vectors in which an anther-specific promoter is operatively linked to a DNA sequence which encodes a polypeptide selected from the group consisting of the coding sequence from the DTA, TURF-13, pectate lyase, gin recombinase, iaaL or cytA toxin genes.

In order to direct the location of the peptide encoded by the recombinant DNA sequence, the recombinant DNA sequence of the present invention may comprise, in a 5' to 3' direction, an anther-specific promoter region operably linked to a signal sequence, which is operably linked to a coding DNA sequence.

Another embodiment of the present invention comprises plasmids containing anther-specific promoter sequences of the present invention. These plasmids include pCIB3132, pCIB3132B, pCIB3178, pCIB3179, and pLC251. The present invention also includes promoter fragments derived from the plasmids of the present invention. For the purpose of the present invention, the term "derived from" a plasmid refers to the physical isolation of a nucleotide sequence or fragment from a plasmid, as well as the physical isolation of a nucleotide sequence or fragment using a probe homologous to one of the above plasmids, or a synthetic nucleotide sequence prepared by using some or all of the nucleotide sequences of the above plasmids.

Another embodiment of the present invention comprises transgenic plants which have been transformed with a recombinant, or chimeric, DNA sequence comprising an anther-specific promoter operatively linked to the coding DNA sequence. Such transgenic plants will express the polypeptide coded by the chimeric DNA sequence only in the anther of the plant. When the polypeptide encoded is a polypeptide which will disrupt formation of viable pollen when expressed in the anther cells, the transgenic plant will not be able to produce viable pollen cells, and hence will be male sterile. For example, such transgenic plants may encode for DTA, TURF-13, pectate lyase, gin recombinase, iaaL or cytA toxin.

DESCRIPTION OF THE SEQUENCES

Sequence 1 is the nucleotide sequence of anther-specific cDNA clone ant32.

Sequence 2 is the amino acid sequence of the polypeptide encoded by the ant32 nucleotide sequence of Sequence 1.

Sequence 3 is the nucleotide sequence of anther-specific cDNA clone ant43D.

Sequence 4 is the amino acid sequence of the polypeptide encoded by the ant43D nucleotide sequence of Sequence 3.

Sequence 5 is the nucleotide sequence of anther-specific cDNA clone ant9.

Sequence 6 is the amino acid sequence of the polypeptide encoded by the ant9 nucleotide sequence of Sequence 5.

Sequence 7 is the nucleotide sequence of anther-specific cDNA clone ant52.

Sequence 8 is the amino acid sequence of the polypeptide encoded by the ant52 nucleotide sequence of Sequence 7.

Sequence 9 is the nucleotide sequence of anther-specific cDNA clone ant59.

Sequence 10 is the amino acid sequence of the polypeptide encoded by the ant59 nucleotide sequence of Sequence 9.

Sequence 11 is the nucleotide sequence of anther-specific cDNA clone ant66.

Sequence 12 is the amino acid sequence of the polypeptide encoded by the ant66 nucleotide sequence of Sequence 11.

Sequence 13 is the nucleotide sequence of anther-specific cDNA clone ant67.

Sequence 14 is the nucleotide sequence of anther-specific cDNA clone ant68.

Sequence 15 is the amino acid sequence of the polypeptide encoded by the ant68 nucleotide sequence of Sequence 14.

Sequence 16 is the nucleotide sequence of the Ant32 genomic clone. This sequence shows the nucleotide sequence of the ant32 gene, including 2.0 kb of 5' flanking sequence. The TATA box is found at bases 1971 to 1975. The putative transcription start site is found at base 2009. Bases 2009 to 2075 comprise the untranslated leader sequence. The ATG translational initiation codon is found at bases 2076 to 2078. No introns are present. The TGA stop codon is found at bases 3420 to 3422.

Sequence 17 is the amino acid sequence of the polypeptide encoded by the Ant32 nucleotide sequence of Sequence 16.

Sequence 18 is the nucleotide sequence of the Ant43D genomic clone. This sequence shows the nucleotide sequence of the ant43D gene, including approximately 1.2 kb of 5' flanking sequence. The putative transcriptional start site is found at base 1167. An unusually long TATA box is found at bases 1089 to 1147. The sequence "TA" is repeated 29 times. The untranslated leader is found between bases 1167 and 1229. The translational initiation codon occurs at bases 1230 to 1232. Translated sequences are shown in uppercase. One intron occurs at bases 1571 to 1668.

Sequence 19 is the amino acid sequence of the polypeptide encoded by the Ant43D nucleotide sequence of Sequence 18.

Sequence 20 is the nucleotide sequence of anther-specific cDNA clone ant43C.

Sequence 21 is the amino acid sequence of the polypeptide encoded by the ant43C nucleotide sequence of Sequence 20.

The arrow indicates the location of the ant32 gene, as well as its 5' to 3' orientation in genomic subclone pCIB950. The promoter region extends from the upstream PstI site to the coding region.

Figure 2:
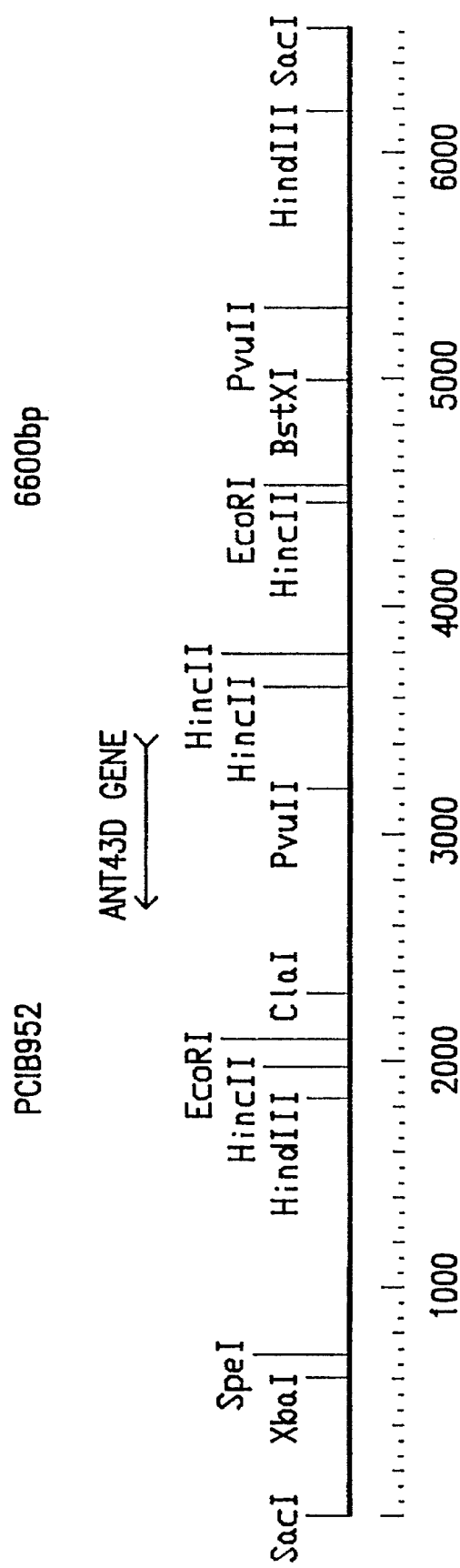

FIG. 2: Restriction map of Ant43D genomic clone pCIB952

The arrow indicates the location of the ant43D gene, as well as its 5' to 3' orientation in genomic subclone pCIB952. The promoter region extends from the upstream EcoRI site to the coding region.

Figure 3A:
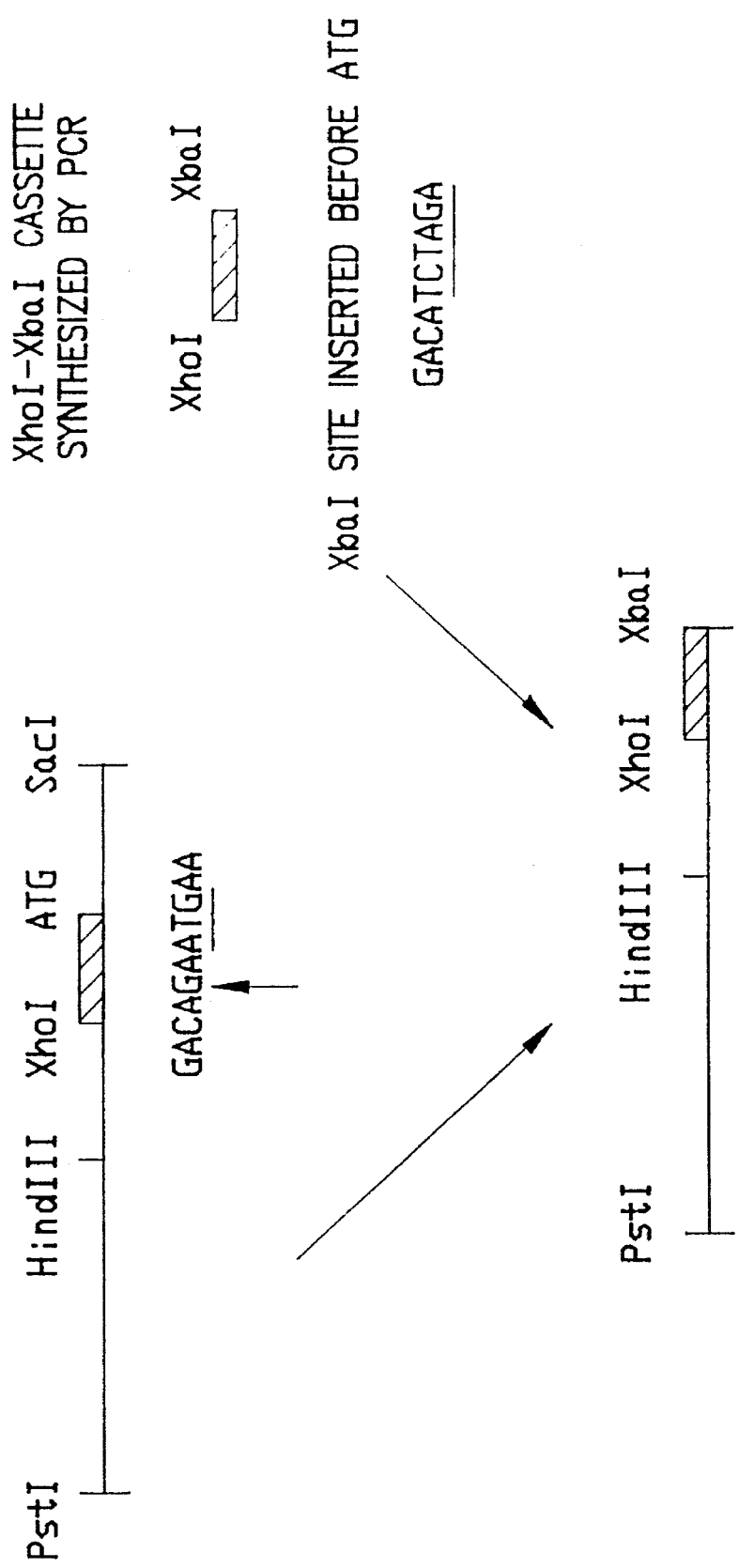
Figure 3B:
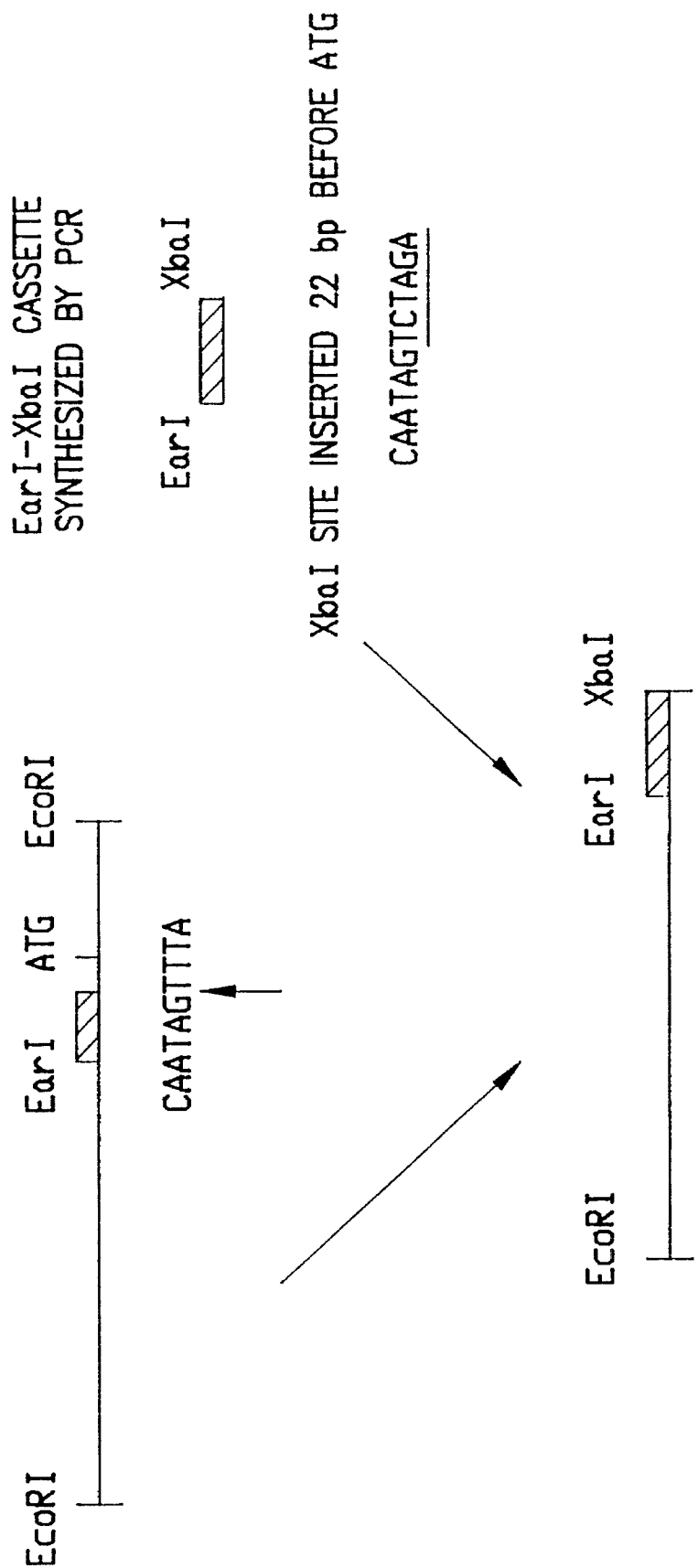

FIG. 3A and 3B: Site-specific mutagenesis via PCR resulting in insertion of a XbaI site before the start of translation of Ant32 (FIG. 3A) and Ant43D (FIG. 3B).

In FIG. 3A, the drawing on the top left shows the 3' end of the PstI-SacI ant32 genomic subclone containing the promoter. Underneath it is the sequence at the ATG before which an XbaI site was inserted as follows: a 350 bp XhoI-XbaI fragment (top right of figure) was synthesized using polymerase chain reaction (PCR) technology (see Mullis et al., *Meth. Enzymology*, 155:335–350 (1987); Erlich (Ed.), *PCR Technology*, Stockton Press (New York 1989)) to copy the ant32 promoter sequence from 55 bp before the unique XhoI site to two bp before the ATG. One of the PCR primers inserted an XbaI site 2bp before the ATG. A full-length ant32 promoter consisting of the PstI-XhoI fragment from the original clone and the XhoI-XbaI PCR cassette was reassembled in a 3-way ligation into the PstI-XbaI sites of the Bluescript vector pBluescript SK (Stratagene). This promoter clone can be used for transcriptonal fusions to coding sequences.

In FIG. 3B, the drawing on the top left shows the 3' end of the EcoRI ant43D genomic subclone containing the promoter. Underneath it is the sequence at the ATG before which an XbaI site was inserted as follows: a 210 bp EarI-XbaI fragment (top right of figure) was synthesized by PCR in order to copy the ant43D promoter from 39 bp before the EarI site to 22 bp before the ATG. One of the PCR primers inserted an XbaI site 22 bp before the ATG. A full-length ant43D promoter consisting of the EcoRI-EarI fragment from the original clone and the EarI-XbaI PCR cassette was reassembled in a 3-way ligation into the EcoRI-XbaI sites of bluescript. This promoter clone can be used for transcriptional fusions to coding sequences.

Figure 4A:
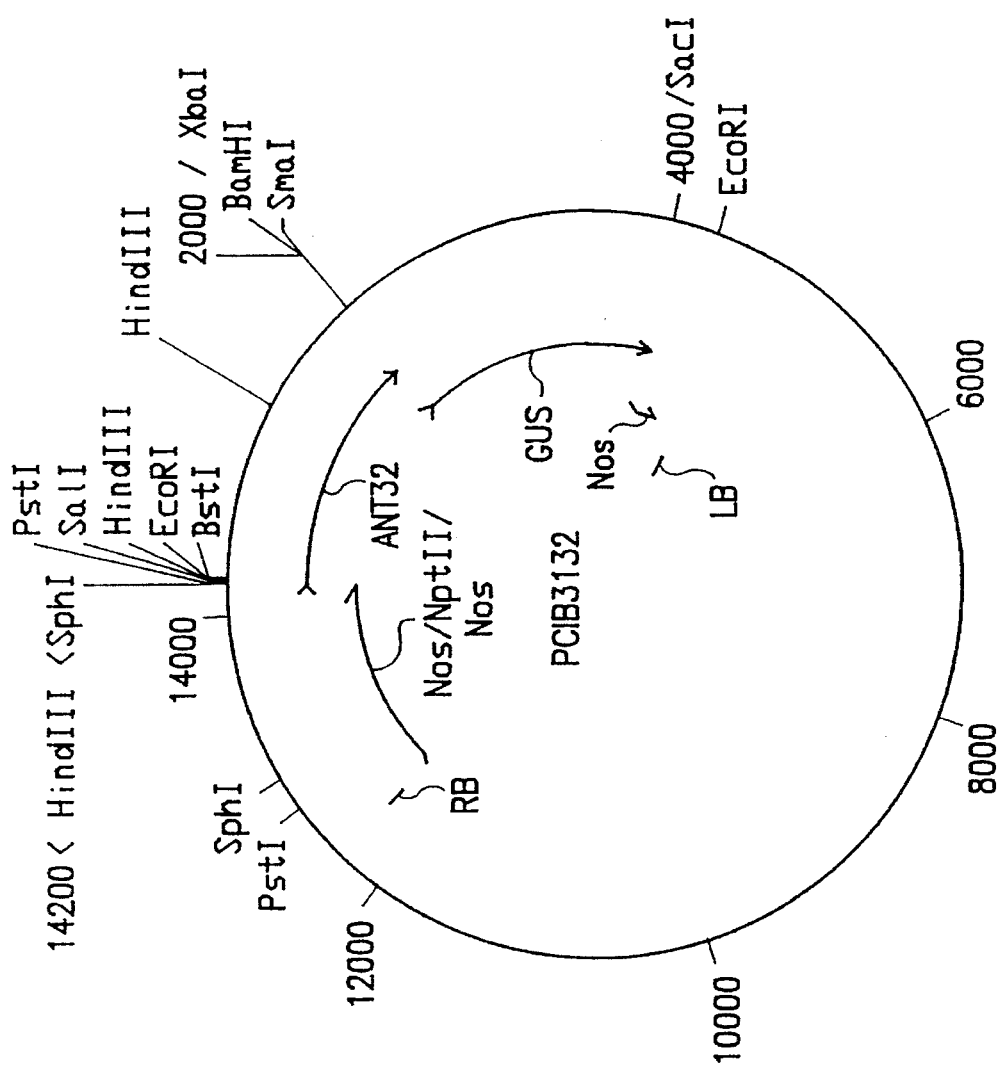
Figure 4B:
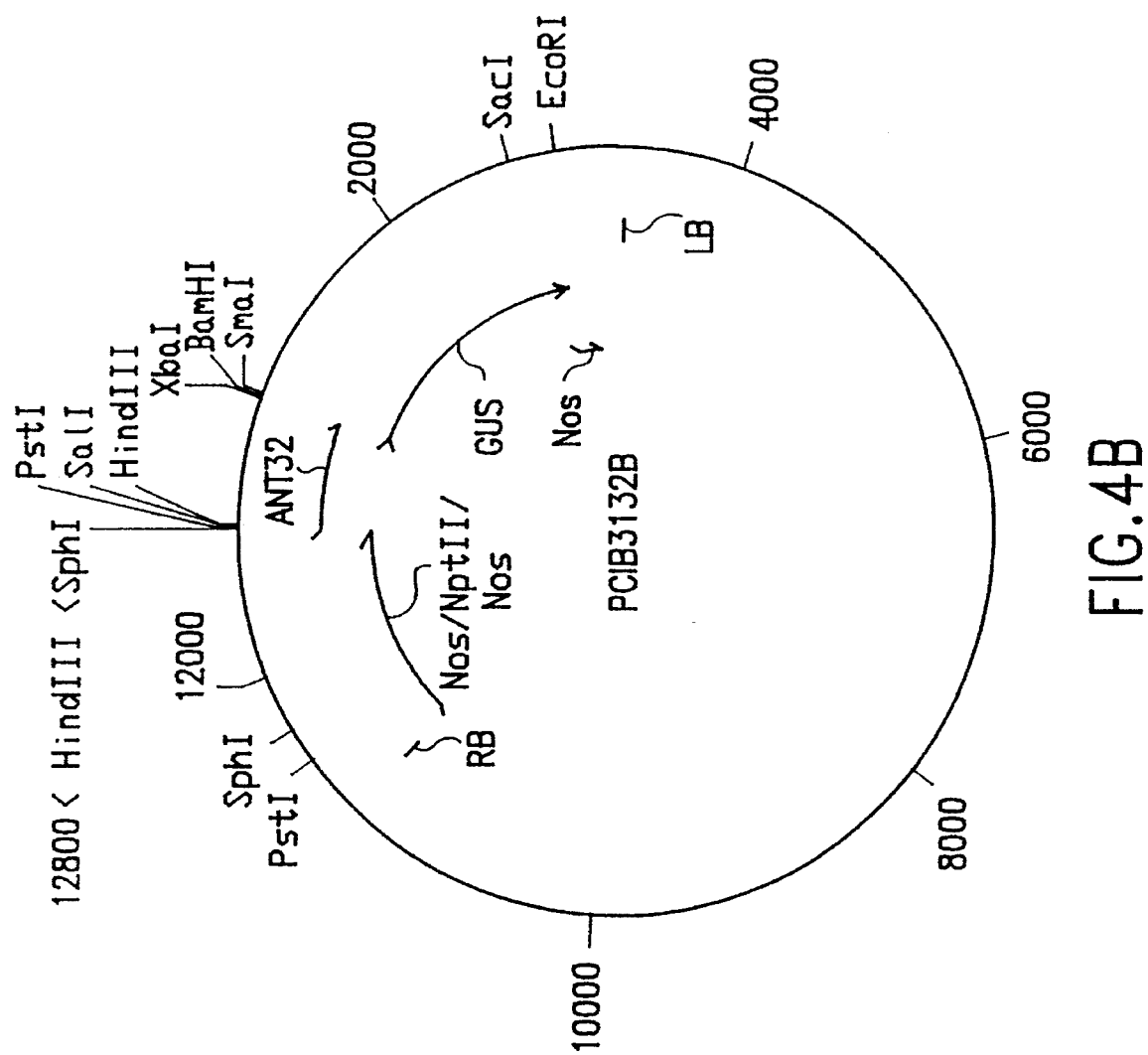

FIG. 4A and 4B: Plasmid maps of Ant32-GUS fusions pCIB3132 (2.0 kb promoter— FIG. 4A) and pCIB3132B (600 bp promoter— FIG. 4B), pCIB3132 has been deposited with the USDA Agricultural Research Service Culture Collection, Northern Regional Research Center (NRRL) at 1815 North University Street, Peoria, Ill. 61604, on Jun. 16, 1992 and has been accorded deposit no. NRRL B-18977.

Figure 5:
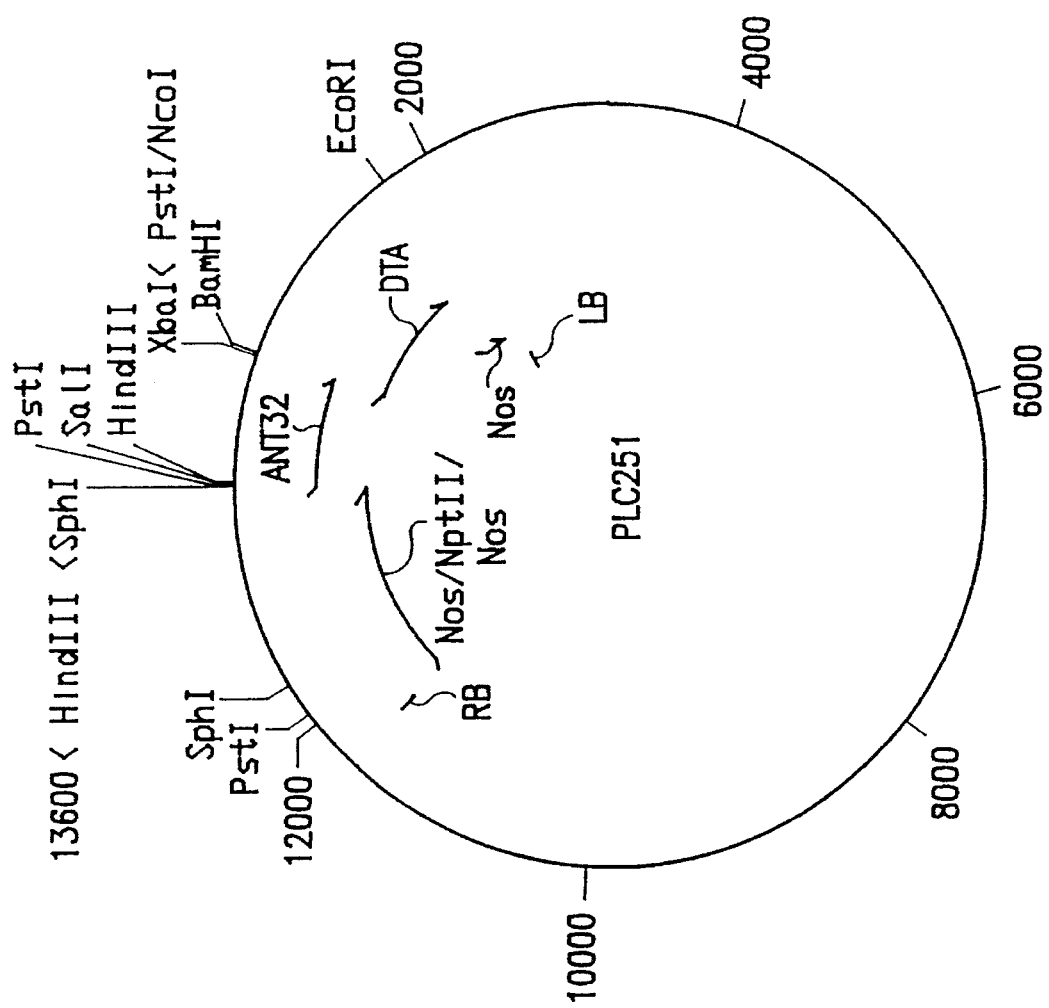

FIG. 5: Plasmid map of Ant32-DTA fusion pLC251

Figure 6:
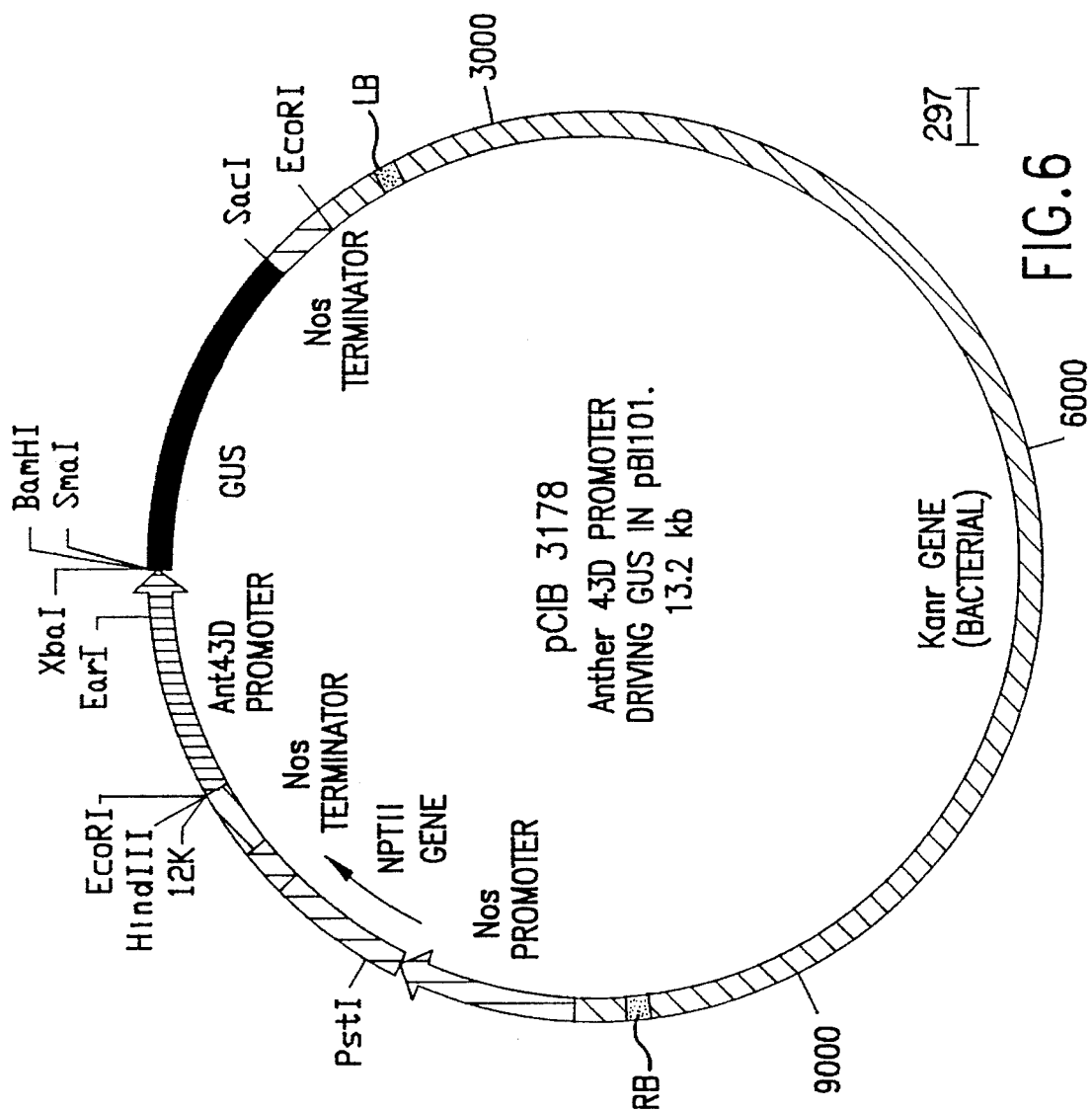

FIG. 6: Plasmid map of Ant43D-GUS fusion pCIB3178. pCIB3178 has been deposited with the USDA NRRL on Jun. 16, 1992 and has been accorded deposit no. NRRL B-18978.

Figure 7:
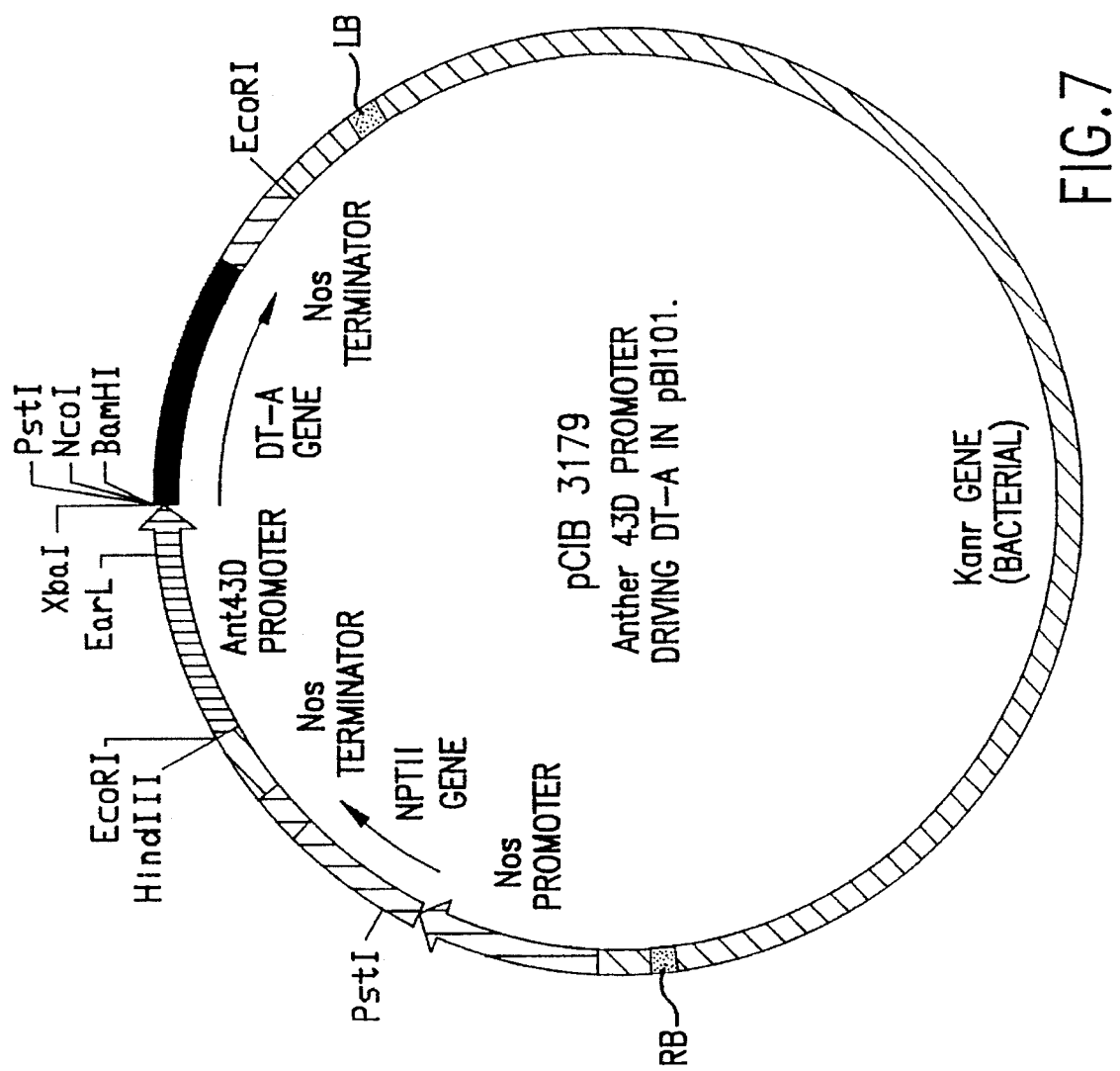

FIG. 7: Plasmid map of Ant43D-DTA fusion pCIB3179

DETAILED DESCRIPTION OF THE INVENTION

Definitions

"Anther-specific" is used to describe cDNAs, genomic DNAs, messenger RNAs, promoter DNA sequences and genes which are associated with anther tissue. In the case of cDNAs, genomic DNAs and messenger RNAs, "anther-specific" describes the fact that, when assayed through northern blot hybridization, the mRNA corresponding to the cDNA, genomic DNA or mRNA sequence is present in anther tissue in concentrations at least about 100-fold that observed in other tissues. In the case of promoter DNA sequences, "anther-specific" describes a regulatory sequence which directs the transcription of associated coding sequences so that the corresponding messenger RNA is present in anther tissue in concentrations at least about 100-fold that observed in other tissues. In the case of a gene, "anther-specific" describes a gene which is expressed in a manner so that the gene product is present in anther tissue in concentrations at least about 100-fold that observed in other tissues. Because anther and pollen tissue are both involved in the male sexual function of a plant, a DNA sequence or gene may be considered to be "anther-specific" for the purpose of the present invention if it is expressed specifically in pollen as well as in anther tissues.

"Recombinant" and "chimeric" are both used to indicate that a DNA sequence, vector or gene is comprised of more than one DNA sequence of distinct origin which have been fused or ligated together, resulting in a DNA sequence, vector or gene which does not occur naturally. For example, the ligation of a promoter DNA sequence from an anther-specific gene with the coding DNA sequence of a different gene is said to be "recombinant" or "chimeric".

The present invention relates to anther-specific nucleotide sequences which are expressed in much higher amounts in the anther of a plant than in other tissue. In one embodiment, the present invention comprises isolated anther-specific cDNA clones ant32, ant43D, ant9, ant52, ant59, ant66, ant67, ant68 and ant43C, corresponding to the sequences of SEQ ID No. 1, SEQ. ID No. 3, SEQ. ID No. 5, SEQ. ID No. 7, SEQ. ID No. 9, SEQ. ID No. 11, SEQ. ID No. 13, SEQ. ID No. 14 and SEQ. ID No. 20, respectively.

In another embodiment, the present invention comprises isolated anther-specific genomic DNA clones which correspond to the anther-specific cDNA clones of SEQ. ID Nos. 1, 3, 5, 7, 9, 11, 13, 14 and 20 above. The genomic DNA clones are isolated using the anther-specific cDNA clones as probes to pull out the corresponding genomic DNA clones. Corresponding genomic DNA clones are those which are transcribed to form a messenger RNA which is complementary to and transcribed into a given cDNA. In a particular embodiment, the present invention comprises the isolated anther-specific genomic DNA clones ant32 and ant43D, the sequences of which are provided at SEQ. ID No. 16 and SEQ. ID No. 18, respectively.

The present invention further comprises recombinant DNA sequences comprising, in a 5' to 3' direction, a promoter region from an anther-specific genomic DNA sequence, which is operatively linked to a coding DNA sequence. The recombinant DNA sequences result in anther-specific expression of the coding DNA sequence. In a preferred embodiment, the coding DNA sequence encodes a polypeptide which, when expressed in the anther cells, will disrupt formation of viable pollen. Preferred as the coding DNA sequence are sequences which encode a polypeptide selected from the group consisting of DTA, TURF-13, pectate lyase, gin recombinase, iaaL and cytA toxin.

The recombinant DNA sequences of the present invention may comprise, in a 5' to 3' direction, a promoter region from an anther-specific genomic DNA sequence, operatively linked to a signal sequence, which is operatively linked to a coding DNA sequence. The signal sequence is responsible for specialized transport of the associated peptide.

The present invention also comprises transgenic plants which have been transformed with a recombinant DNA sequence comprising the promoter region from an anther-specific genomic DNA sequence.

The anther-specific cDNA sequence of the present invention is obtained by preparing cDNA libraries from anther tissue and leaf tissue. Single stranded DNA from the leaf is photobiotinylated and hybridized to the anther DNA. Photobiotinylated DNA is removed, leaving a library enriched for anther-specific cDNA sequences. (Example 3). Anther-specific cDNAs are identified by differential screening (Example 4)). The anther-specific cDNAs are cross-hybridized to identify unique cDNAs. (Example 4). Anther-specific expression is verified by RNA blot hybridization with various plant tissues and in situ hybridization. (Examples 5 and 8). Developmental expression, sequences and gene copy number of the anther-specific cDNA clones is also determined. (Examples 6 and 7 and 9).

The cDNA sequences of the present invention can be used to isolate genomic DNA sequences. Where a partial cDNA has been obtained, the partial cDNA is used as a probe to screen the anther cDNA library in order to isolate a full length cDNA clone. Hybridizing clones are purified, restriction mapped and sequenced. A full length clone will be near message size as well as having a complete open reading frame. To isolate a genomic clone, the full length anther cDNA is used as a probe to screen a genomic library. By restriction mapping and hybridization to the anther cDNA, the coding region of the genomic clone is identified. The area upstream from the coding area of the clone is the anther promoter region.

The anther promoter region may be more precisely mapped through deletion analysis. 5' deletions of an anther promoter are made by introducing restriction sites by PCR using oligonucleotide primers with restriction sites at the 5' ends and anther promoter sequences at the 3' ends. The PCR products are digested, purified, and cloned into pBI101 (Clontech). The deletion mutants contain the 5' untranslated leader sequence fused to the translational start site of the GUS gene. Internal and 3' deletions of anther promoters are made by PCR in a similar manner. The PCR fragments are fused to a GUS vector containing the CAMV 35S minimal promoter (–46 to +1, Benfey et al., EMBO 9: 1677–1684 (1990)). Transgenic plants are tested with the GUS fluorometric and histochemical assay.

The signal sequence of the present invention may be any DNA sequence which is able to direct the transport of an associated polypeptide. The signal sequence is preferably a sequence which is translated into a signal peptide, which becomes separated from the peptide after transit of the peptide is complete. Signal sequences are useful for directing the polypeptide product of the coding DNA sequence to a desired location within the cell, such as to the mitochondria or to the endoplasmic reticulum, or to direct extracellular transport outside of the cell. Among the signal sequences useful for the present invention are, for example, the signal sequence from the pathogenesis-related gene (PR-1) of tobacco, which is described in Cornellisen et al., EMBO 5:37–40 (1986); the yeast mitochondrial presequence; Schmitz et al., Plant Cell, 1:783–791 (1989); the signal sequence from plant mitochondrial Rieske iron-sulfur protein, Huang et al., PNAS USA Vol 88, 10716–10720 (1991); mitochondrial and chloroplast targeting peptides, von Heijne et al., Eur. J. Biochem., 180:535–545 (1989). The identification of other leader sequences is known in the art. See Della-Cioppa et al., Plant Physiology, 84:965–968 (1987); Schekman, TIBS, 188 (1985).

The coding DNA sequence of the present invention may be any DNA sequence encoding for a desired polypeptide. Preferred for use in the present invention are coding DNA sequences which encode the production of a polypeptide which, when expressed in anther tissue, will result in the inability of the plant to produce viable pollen. Examples of such coding DNA sequences include the genes which are described in the following references, the disclosures of which are hereby incorporated by reference as if fully set forth herein:

a) Diptheria toxin A-chain gene (DTA), which inhibits protein synthesis, Greenfield et al., PNAS USA, 80: 6853 (1983); Palmiter et al., Cell, 50: 435 (1987).

b) Pectate lyase gene pelE from *Erwinia chrysanthemi* EC16, which degrades pectin, causing cell lysis. Keen et al., J. Bacteriology, 168:595 (1986).

c) Turf13 (TURF-13) gene from cms-T maize mitochondrial genomes; this gene encodes a polypeptide designated URF13 which disrupts mitochondrial or plasma membranes. Braun et al., Plant Cell, 2:153 (1990); Dewey et al., PNAS USA, 84:5374 (1987); and Dewey et al., Cell, 44:439 (1986).

d) Gin recombinase gene from phage Mu gene, which encodes a site-specific DNA recombinase which will cause genome rearrangements and loss of cell viability when expressed in cells of plants. Maeser et al., Mol. Gen. Genet., 230:170–176 (1991).

e) Indole acetic acid-lysine synthetase gene (iaaL) from *Pseudomonas syringae*, which encodes an enzyme that conjugates lysine to indoleacetic acid (IAA). When expressed in the cells of plants, it causes altered development due to the removal of IAA from the cell via conjugation. Romano et al., Genes and Development, 5:438–446 (1991); Spena et al., Mol. Gen. Genet., 227:205–212 (1991); Roberto et al., PNAS:USA, 87:5795–5801 (1990).

f) CytA toxin gene from *Bacillus thuringiensis Israeliensis* which encodes a protein that is mosquitocidal and hemolytic. When expressed in plant cells, it causes death of the cell due to disruption of the cell membrane. McLean et al., J. Bacteriology, 169:1017–1023 (1987); Ellar et al., U.S. Pat. No. 4,918,006 (1990).

EXAMPLES

EXAMPLE 1: Plant Material and Growth Conditions

Tobacco plants (*Nicotiana tabacum* cv Xanthi) are grown from seed in Metromix in a greenhouse under a 16-hour light/8-hour dark light regime.

EXAMPLE 2: Anther and Leaf mRNA Isolation

Total RNA is isolated from anthers from 0 to 10 mm pistil length flower buds and from 5 week old seedlings by the Phenol/SDS method described by Ausubel et al., Current Protocols in Molecular Biology, John Wiley and Sons, NY (1987). PolyA+ RNA is purified from total RNA as described by Maniatis et al., Molecular Cloning: A Laboratory Manual, Cold Spring Harbor Laboratory Press, NY (1982).

EXAMPLES 3: Construction of Subtracted cDNA Libraries

Anther and seedling cDNA libraries are made using Invitrogen's Librarian II kit. Double-stranded cDNA is synthesized from anther and leaf polyA+ RNA, BstXI non-palindromic linkers are ligated on and the cDNA is cloned into a BstXI cut pTZ18R-B vector. Transformation is into *E. coli* DHiαF' cells. A subtraction cDNA library is made using Invitrogen's Subtractor kit. Single-stranded DNA is isolated from the anther and leaf cDNA libraries. The leaf single-stranded DNA is photobiotinylated and hybridized to the anther single-stranded DNA. Both hybridized and unhybridized photobiotinylated sequences are removed with streptavidin and phenol extraction. The remaining DNA is converted to double-stranded form with Klenow and transformed into *E. coli* DHiαF' cells.

EXAMPLE 4: Isolation of Anther-Specific cDNA Clones

Anther-specific clones are identified by differential screening of the anther subtraction cDNA library. 20,000 clones are replica plated onto nitrocellulose filters and differentially screened to identify colonies hybridizing to radioactively labeled first strand cDNA from anther polyA+ RNA but not to first strand cDNA from seedling polyA+. The inserts of 70 cDNAs are differentially screened again by Southern blot. Northern blots of anther, pistil and leaf total RNA are probed with the cDNAs to confirm tissue specificity. All anther-specific cDNAs are cross-hybridized to identify unique cDNAs. Unique cDNA clones are purified and subcloned into bluescript vector.

A full-length cDNA clone of ant32 is isolated by screening the anther cDNA library with a 0.9 kb partial cDNA. The two cDNAs are 95% homologous at the sequence level, and are therefore closely related members of the same gene family.

EXAMPLE 5: Verification of Expression Pattern by RNA Blot Hybridization

Northern blots are done using nitrocellulose filters as described in Maniatis (1982). 20 μg of anther, pistil and leaf total RNA are loaded per lane. Prehybridizations are done at 68° C. for 4 hours in 3X SSC, 5X Denhardt's, 20mM Tris pH 7, 0.1% SDS, 2mM EDTA and 100 μg/ml sheared denatured salmon sperm DNA. Hybridizations are done at 42° C. overnight in 6X SSC, 5X Denhardt's, 0.1% SDS, 500

μg/ml salmon sperm DNA, 8% dextran sulfate and 50% formamide to which 5.5×10⁶ cpm/ml of probe is added. Probes are synthesized using Pharmacia's oligolabelling kit in accordance with the manufacturer's instructions. Expression of the cDNAs is seen only in anther RNA. Expression in pollen is also seen with the ant66 cDNA.

PolyA+ RNA is isolated from anther, pistil, leaf, petal, stem and root tissue. 1 μg of each along with 20 μg of seed and sepal total RNA are run on a Northern and probed with the ant32 and ant43D cDNAs. Expression of both cDNAs is seen only in anther RNA, demonstrating that the ant32 and ant43D cDNAs are tightly regulated and expressed only in anther tissue.

EXAMPLE 6: Developmental Expression of Anther-Specific cDNA Clones

Total RNA is isolated from anthers from 6 stages of flower bud lengths. Slot blots are probed with the anther-specific cDNAs to determine developmental expression. Slot hybridization is done as in Maniatis (1982) using 10 μg of RNA. Table 1 contains the developmental expression profile of the cDNAs. Ant9, 32, 43C, 59, and 68 are expressed only early in anther development, whereas ant43D, 52 and 67 are expressed throughout development. Ant66 is expressed only late in development.

EXAMPLE 7: Sequencing of Anther-Specific cDNA Clones

DNA is sequenced using the dideoxy chain-termination method of Sanger et al. *PNAS USA* 74:5463–5467 (1977), using double-stranded plasmid DNA as a template. All DNA sequence analysis is carried out on a Digital Vax 8530 computer using the University of Wisconsin Computer Genetics Group software. The oligonucleotide primers are synthesized on an Applied Biosystems Model 380A Synthesizer.

Table 1 contains a comparison of message size to insert size of the anther-specific cDNAs. The ant32 and ant43D cDNAs are close to the size expected for full length copies of the mRNAs. The rest of the cDNAs are incomplete clones. Ant32, 43C, 43D, 52, 59, 66 and 68 encode a single open reading frame. The ant32 cDNA is a near full-length clone of 1542 bases (SEQUENCE ID NO. 1). The sequence contains a large open reading frame which extends from nucleotide 66 to 1412, encoding a complete polypeptide of 448 amino acids. The open reading frame is flanked by 5' and 3' non-coding regions of 65 and 130 bases respectively. A polyadenylation signal, AATAAA, occurs at position 1502.

The ant43D cDNA is a near full-length clone of 552 bases (SEQUENCE ID NO. 3). The sequence contains a complete open reading frame of 118 amino acids, extending from bases 41 to 397. The open reading frame is flanked by 40 bases on the 5' end and 155 bases on the 3' end. A polyadenylation signal is found starting at position 437.

Ant43C is an incomplete cDNA of 437 bases (SEQUENCE ID NO. 20). A partial polypeptide of 90 amino acids is encoded by nucleotides 167 to 436. The ant43C cDNA and the ant43D cDNA are 90% homologous at the sequence level.

Ant52, an incomplete cDNA clone of 96 bases (SEQUENCE ID NO. 7) contains an open reading frame of 31 amino acids.

Ant59 is an incomplete cDNA clone of 1201 bases (SEQUENCE ID NO. 9). An open reading frame extending from nucleotide 1 to 1119 encodes a partial polypeptide of 372 amino acids. The open reading frame is flanked by a 3' non-coding region of 82 bases.

Ant66 is an incomplete cDNA clone of 952 bases (SEQUENCE ID NO. 11). A partial polypeptide of 236 amino acids is encoded by nucleotides 1 to 711. The open reading frame is flanked by a 3' region of 241 bases. The sequence contains a polyA tail of 15 bases.

Ant68 is an incomplete cDNA clone of 445 bases (SEQUENCE ID NO. 20. An open reading frame of 148 amino acids is encoded by the sequence.

Ant67 is an incomplete cDNA clone of 305 bases (SEQUENCE ID NO. 13). It is unknown which strand is the sense strand since a single large open reading frame was not found. This clone contains the 3' end of an open reading frame and a 3' flanking region in translations of both strands.

Ant9 is an incomplete, chimeric cDNA of 612 bases (SEQUENCE ID NO. 5). Northerns of anther, pistil, and leaf tissue are probed with 5' and 3' regions of the chimeric cDNA to determine the anther-specific region of the cDNA clone. Northerns probed with bases 1 to 325 hybridize to anther, pistil and leaf tissue. This region of the cDNA encodes an open reading frame. Northerns probed with bases 326 to 612 hybridize exclusively to anther tissue. This region is identified as the anther-specific region of the chimeric cDNA. A partial polypeptide of 32 amino acids is encoded by nucleotides 344 to 442. A polyadenylation signal starts at position 461.

Each deduced amino acid sequence is compared to sequences in Genbank. The ant66 cDNA had a 74% overall amino acid identity with a plasma membrane proton ATPase (H+-ATPase) from *Arabidopsis thaliana*. Harper et al., *PNAS* 86:1234–1238 (1989). The ant68 cDNA encodes a glycine-rich protein.

EXAMPLE 8: Verification of Ant32 Expression Pattern by In-Situ Hybridization In situ hybridization studies with paraffin-embedded anther sections from 12mm long flower buds are carried out as described by Perez-Grau et al., *Plant Cell* 1, 1095–1109. ³⁵S-RNA probes used for in situ hybridizations are synthesized using Stratagene's RNA Transcription Kit. Cross sections and longitudinal sections are probed with ant32 antisense and sense RNA probes. Expression is localized in the tapetal cell layer of the anther with the antisense probe.

EXAMPLE 9: Gene Copy Number

In order to determine how many genes in the tobacco genome hybridize with the anther-specific genes, Xanthi genomic DNA was digested with XbaI, HindIII, EcoRI, and BamHI. Southern blots are probed with the cDNA clones. The blots probed with ant32, 43, 52, 59 and 67 had 2 bands hybridizing in each digest, indicating that these cDNAs are single copy genes or members of small gene families. More bands per digest hybridized in the blots probed with ant9, 66 and 68, indicating that these cDNAs are members of larger gene families.

EXAMPLE 10: Southern Blots

Southern blots are done with nitrocellulose as described in *Maniatis* (1982). Prehybridizations are in 6X SSC, 10X Denhardt's, 0.2% SDS, and 75 μg/ml salmon sperm DNA at 68° C. for 4 to 6 hours. Hybridizations are done at 68° C. in 6X SSC, 5X Denhardt's, 0.5% SDS and 125 μg/ml salmon sperm DNA to which 1×10⁶ cpm/ml DNA probe is added.

Washes are as described in *Maniatis* (1982). Genomic Southern blots are done with Duralon-UV membranes (Stratagene) and hybridization conditions are as in the manufacturer's directions.

EXAMPLE 11: Construction of Tobacco Genomic DNA Libraries

Tobacco DNA is isolated from leaves using the method of Shure et al., *Cell* 35:225–233 (1983). Sau3AI partial digests of Xanthi genomic DNA are cloned into the BamHI site of Stratagene's Lambda DashII vector and the library is amplified. Another genomic library is made using Promega's LambdaGEM-11XhoI Half-Site Arms Cloning System. Partially filled-in Sau3AI digested genomic DNA is cloned into partially filled-in XhoI LambdaGEM-11 arms.

EXAMPLE 12: Isolation and Sequencing of the Ant32 Genomic Clone

Figure 1:
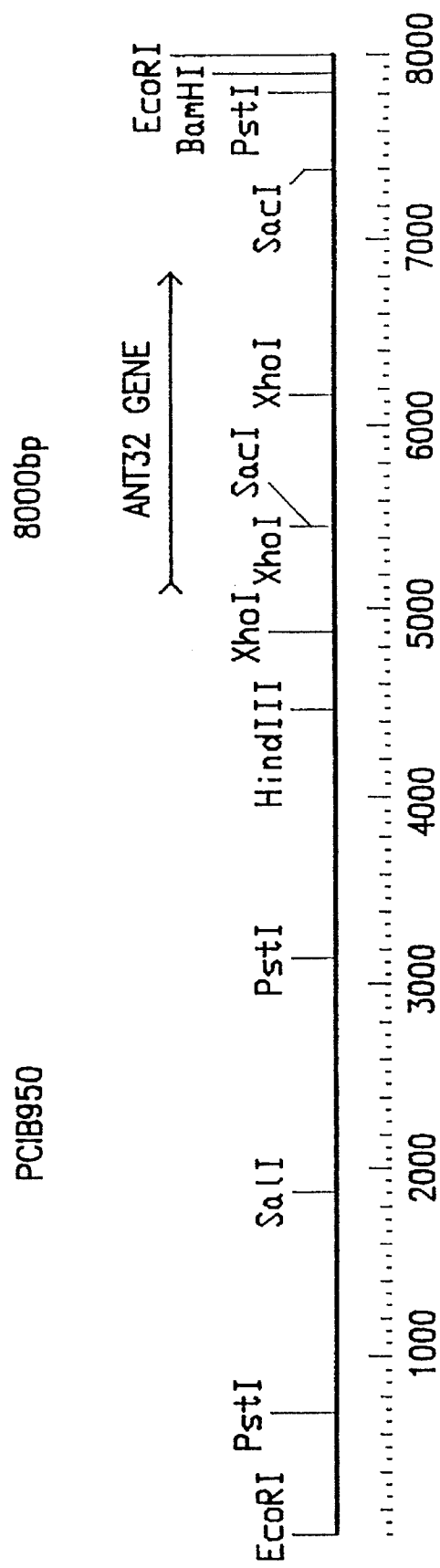
FIG. 1: Restriction map of Ant32 genomic clone pCIB950

The amplified Stratagene genomic library is screened with ant32 as a probe, yielding 4 hybridized placques. All four clones are purified and restriction mapped. When probed with ant32, one EcoRI fragment from each clone hybridized. Subcloning and mapping of the EcoRI fragments from the 4 clones showed that 2 are identical. FIG. 1 contains the map of EcoRI subclone pCIB950. Fragments from pCIB950 are then subcloned for sequencing. 2.0 kb of promoter, the entire coding region, and 0.28 kb of 3' untranslated region is sequenced. The 2.0 kb promoter fragment from ant32 is functional. As shown in Example 16, a 0.6 kb fragment from ant32 is sufficient to confer anther specific activity.

EXAMPLE 13: Isolation and Sequencing of the Ant43D Genomic Clone

The Lambda GEM-11 primary library is screened with ant43D as a probe. Hybridizing placques are rescreened by PCR to distinguish between ant43D and ant43C, a closely related cDNA. PCR fragments generated from the placques are digested to distinguish between genomics correlating to the 2 cDNAs. Two genomic clones correspond to ant43D, and they are purified and mapped. A 6.6 kb SacI band from both hybridizes to an ant43D probe. Subcloning and mapping of both SacI bands shows that they are identical. FIG. 2 contains the map of the SacI subclone, pCIB952. Fragments from pCIB952 are subcloned and sequenced. 1.2 kb of promoter, the entire coding region including one intron, and 0.22 kb of 3' untranslated region is sequenced. The 1.2 kb promoter fragment contains the entire ant43D promoter.

EXAMPLE 14: Primer Extension

The primer is end-labeled using [λ-$^{32}$P] ATP (6000 Ci/mmole, Amersham) and T4 polynucleotide kinase. 20 μg of anther total RNA is mixed with 0.01 pmole of primer in 20 μl of reverse transcriptase buffer (50 mM Tris pH8.3, 75 mM KCl, 3 mM MgCl$_2$). The mixture is heated at 80° C. for 10 min, annealed by slowly cooling to 40° C. and hybridized overnight at 40° C. To each 20 μl reaction is added 30 μl of 5 mM DTT, 0.1 mg/ml BSA, 1 mM each of dATP, dCTP, dGTP, and dTTP in reverse transcriptase buffer containing 200 units of RNAsin (Promega) and 400 units of MMLV reverse transcriptase (BRL). Primer extension is carried out at 40° C. for 60 min. The DNA/RNA hybrid is extracted once with phenol:chloroform and ethanol precipitated in the presence of carrier DNA. The pellet is dissolved in sequencing loading dye and analyzed on a 6% acrylamide-urea sequencing gel.

EXAMPLE 15: Mapping the Transcript Start Site by Primer Extension

The start of transcription of the ant32 cDNA and the ant43D cDNA are mapped using primer extension. The largest primer extension product falls within a few base pairs of the end of the ant32 cDNA. The largest primer extension product falls 23 base pairs upstream of the end of the ant43D cDNA.

EXAMPLE 16: Fusions of the ant32 promoter sequence to the GUS gene

The 2.0 kb 5' flanking region of pCIB950 containing the ant32 promoter is fused to the bacterial reporter gene for glucuronidase (GUS) in order to characterize the promoter of the anther-specific gene in transgenic plants. An XbaI site is inserted before the ATG by PCR as described in FIG. 3A, and the promoter is reassembled in a 3-way ligation into the Bluescript vector. The resulting promoter is excised as a SalI — XbaI fragment and fused to the GUS gene in pBI101 (Clontech). A 600 base pair ant32 promoter — GUS fusion is constructed by deleting a 1.4 kb HindIII fragment from the bluescript promoter clone. The deleted promoter is excised as a SalI — XbaI fragment and fused to the GUS gene in pBI101. The 2.0 kb promoter-GUS fusion is designated pCIB3132 and the 0.6 kb promoter-GUS fusion is designated pCIB3132B. The 0.6 kb promoter fragment from ant32 is sufficient to confer anther specific activity.

EXAMPLE 17: Fusion of the ant32 promoter sequence to the DTA gene

A chimeric gene is constructed using a 5' ant32 promoter sequence and the Diptheria toxin A-chain (DTA) coding sequence (Palmiter et al., *Cell* 50, 435–443). The GUS coding sequence is excised from pCIB3132B with SmaI and SacI, the SacI site is filled in, and the plasmid is religated back together (pLC250). The DTA coding sequence is ligated as a BglII fragment into the BamHI site of pLC250, resulting in pLC251. The DTA coding sequence is fused in the opposite orientation in pLC252.

EXAMPLE 18: Fusion of the ant43D promoter sequence to the GUS gene

The 1.2 kb 5' flanking region of the ant43D gene is fused to GUS. An XbaI site is inserted before the ATG by PCR as shown in FIG. 3B, and the promoter is reassembled in a 3-way ligation in bluescript. The resulting promoter is excised as a HindIII-XbaI fragment and fused to the GUS gene in PBI101 (pCIB3178). FIG. 3B demonstrates how the 1.2 kb flanking region of the ant43D gene is obtained. The 1.2 kb promoter fragment is sufficient to confer anther specific activity.

EXAMPLE 19: Fusion of the ant43D promoter sequence to the DTA gene

The 1.2 kb ant32 promoter is excised from pLC251 with HindIII-XbaI and replaced with a HindIII-XbaI ant43D promoter fragment. The resulting plasmid is designated pCIB3179.

The DTA coding sequence is fused in the opposite orientation in pCIB3188. The ant32 promoter is excised with HindIII and XbaI from pLC252 and replaced with the ant43D promoter.

EXAMPLE 20: Production of Transgenic Plants

Tobacco leaf discs are transformed with the ant32-GUS (pCIB3132 (2 kb promoter) and pCIB3132B (0.6 kb promoter)), ant32-DTA (pLC251 and antisense control (pLC252)), ant43D-GUS (pCIB3178), and ant43D-DTA (pCIB3179 and antisense control (pCIB3188)) constructions and mature transformed plants selected as in Horsch et al., *Science* 227:1229–1231 (1985). The presence of transforming DNA is confirmed using PCR.

EXAMPLE 21: GUS Analysis of ant32 Transgene Expression

Transformants are tested by the GUS histochemical assay as in Koltunow et al., *Plant Cell* 2:1201–1224 (1990) and fluorometrically as in Jefferson, *Plant Molecular Biology Reporter* 5:387–405 (1987). In the histochemical assay, GUS expression is seen in the tapetal cell layer of the anthers of flower buds 10 to 20 mm long. Expression is also seen in pollen to a lesser extent. Anther, pistil, pollen, leaf and stem tissue are assayed fluorometrically and GUS activity is limited to anther and pollen tissue.

EXAMPLE 22: Analysis of ant32-DTA Transgenic Plants

The flower morphology of 13 transgenic plants containing pLC251 and 15 plants of pLC252 is observed. The plants containing pLC251 all had brown, withered anthers and no pollen shed. In contrast, pLC252 transgenic plants had normal anthers and pollen shed. Selfs and backcrosses are done on all plants. In the pLC251 plants, no self pollinations are obtained, but seeds are obtained from backcrosses. Fertility in self and backcross pollinations is normal for pLC252 plants.

Anthers from 14–16 mm and 25–30 mm long flower buds are fixed, embedded in paraffin, and sections are stained with toluidine blue. The tapetum and pollen sac are destroyed in pLC251 plants, whereas pLC252 plants had normal morphology.

EXAMPLE 23: GUS Analysis of ant43D Transgene Expression

Transformants are tested by the GUS histochemical and fluorometric assays. In the histochemical assay, GUS expression is seen in the tapetal cell layer of anthers of buds 14 to 16 mm long, in microspores, and increasingly in the connective and wall tissue of the anther. Anther, pollen, pistil, leaf, sepal, stem and root tissue are assayed fluorometrically. GUS activity is limited to anther and pollen tissue.

EXAMPLE 24: Analysis of ant43D-DTA Transgenic plants

The flower morphology of 8 pCIB3179 plants and eight plants of the control pCIB3188 (DTA in antisense orientation) is observed. The pCIB3179 transgenic plants all had nonfunctional anthers as no pollen was shed. Anther size among different plants ranged from normal to shrunken, anther color from green to brown, and anthers from dehiscent to nondehiscent. The control pCIB3188 transgenic plants had normal anther morphology and pollen shed. Selfs and backcrosses are done on the plants. In pCIB3179 plants, pollinations from backcrosses are obtained, but self pollinations are not. Fertilization in pCIB3188 plants is normal.

Anthers from 8–10 mm, 10–12 mm, 14–16 mm and 25–30 mm long flower buds are fixed, embedded in paraffin, and sections are stained with toluidine blue. Microspores are absent from pCIB3179 plants as early as in 8–10 mm long buds.

---

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
      ( A ) LENGTH: 1542 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Nicotiana tabacum
      ( C ) INDIVIDUAL ISOLATE: Ant32

( i x ) FEATURE:
      ( A ) NAME/KEY: CDS
      ( B ) LOCATION: 66..1412

( x i ) SEQUENCE DESCRIPTION: SEQ ID NO:1:

```
TCTGTCAAGA    TAACAATAAA   AGAATAAAAA   GATTAACCAA   AAACGATATA   CATATTTAGG         60

ACAGA ATG AAG GTT AGC TTG AAG CAC CAC TGG GTA GTG AAG CCA GCA                       107
```

```
              Met Lys Val Ser Leu Lys His His Trp Val Val Lys Pro Ala
                1               5                  10

GAG GCA ACA TGG AAT GGC ACT GTC TCC TTA TCG GAG TGT GAT CAA ACT           155
Glu Ala Thr Trp Asn Gly Thr Val Ser Leu Ser Glu Cys Asp Gln Thr
 15              20                  25                  30

TTT GCT GTA ACT CAT GTA CCA ACC ATT TAT TAC TAC AGG TTT TGC CAT           203
Phe Ala Val Thr His Val Pro Thr Ile Tyr Tyr Tyr Arg Phe Cys His
                 35              40                  45

GAT TGT CTT CCA TCA ACA GAC AAT ATC ATC AAA ACC CTC AGG ACC TCA           251
Asp Cys Leu Pro Ser Thr Asp Asn Ile Ile Lys Thr Leu Arg Thr Ser
             50                  55                  60

CTA AGC AAA GCA TTA GTA CAC TTC TAT CCA TTG TCT GGT CGT TTG CGA           299
Leu Ser Lys Ala Leu Val His Phe Tyr Pro Leu Ser Gly Arg Leu Arg
         65                  70                  75

TGG ATC GCT GGG TCC CGC CTC GAG CTC GAC TGT AAT GCC TCG GGA ATC           347
Trp Ile Ala Gly Ser Arg Leu Glu Leu Asp Cys Asn Ala Ser Gly Ile
     80                  85                  90

GTG CTC ATG GAA GCT GAA ACC GAA GCC AAA CTA GAT GAT CTT GGC GAT           395
Val Leu Met Glu Ala Glu Thr Glu Ala Lys Leu Asp Asp Leu Gly Asp
 95                  100                 105                 110

TTC TCG CCA TCC CCT GAC TTG AAC AGC TTG TTT CCC CGT GTA GAC TAC           443
Phe Ser Pro Ser Pro Asp Leu Asn Ser Leu Phe Pro Arg Val Asp Tyr
                 115                 120                 125

ACA ATC CCA ATT GAT GAA CTC CCT TTG TTG TTT GTT CAG CTT ACT AAG           491
Thr Ile Pro Ile Asp Glu Leu Pro Leu Leu Phe Val Gln Leu Thr Lys
             130                 135                 140

TTT CAG TGT GGT GGT ATT GCT CTG AGT TTT GCA ATA TCA CAT GCT GTA           539
Phe Gln Cys Gly Gly Ile Ala Leu Ser Phe Ala Ile Ser His Ala Val
         145                 150                 155

GTT GAT GGC CAA AGT GCT CTT TAC TTC CTC ACC GAA TGG GCT AGC CTT           587
Val Asp Gly Gln Ser Ala Leu Tyr Phe Leu Thr Glu Trp Ala Ser Leu
     160                 165                 170

GCT CGC GGA GAG CCA TTA GGG AAC GAA CCT TTT CAT GAT CGA AAA TTC           635
Ala Arg Gly Glu Pro Leu Gly Asn Glu Pro Phe His Asp Arg Lys Phe
 175                 180                 185                 190

CTC CGA GCA GGG GAA CCT CCA ATT GCA TAT CCA ACG TTT GAG CAT TTA           683
Leu Arg Ala Gly Glu Pro Pro Ile Ala Tyr Pro Thr Phe Glu His Leu
                 195                 200                 205

CAG TTT AAT CCA CCA CCA CTT TTG CTT GGA CAG TCC AGC AGT GAA GAG           731
Gln Phe Asn Pro Pro Pro Leu Leu Leu Gly Gln Ser Ser Ser Glu Glu
             210                 215                 220

GAG AAG AAA AAT GAA ACA AAG GGT TCC ATG CTA AAA CTT ACA AAA CAT           779
Glu Lys Lys Asn Glu Thr Lys Gly Ser Met Leu Lys Leu Thr Lys His
         225                 230                 235

CAA GTT GAA ATG TTG AGA AAA AAG GCG AAC CAA GGT AAT CAA GGG CGT           827
Gln Val Glu Met Leu Arg Lys Lys Ala Asn Gln Gly Asn Gln Gly Arg
     240                 245                 250

AGT TAC ACA CGT TAT GAA GTT GTG ACT GCA CAT ATA TGG AGA TGT GCA           875
Ser Tyr Thr Arg Tyr Glu Val Val Thr Ala His Ile Trp Arg Cys Ala
 255                 260                 265                 270

TGC AAG GCA AGA GGT CAT AAA TTT GAG CAG CCT ACT AAT TTA TGC ATT           923
Cys Lys Ala Arg Gly His Lys Phe Glu Gln Pro Thr Asn Leu Cys Ile
                 275                 280                 285

TGT GTT AAC ATA CGC AAT ATA ATG CAA CCA CCT TTG CCT AAA TCC TAT           971
Cys Val Asn Ile Arg Asn Ile Met Gln Pro Pro Leu Pro Lys Ser Tyr
             290                 295                 300

TTT GGC AAT GCC ATA GTT GAT GTT ATT GCC AAT GGC GTC TCG GGT GAC          1019
Phe Gly Asn Ala Ile Val Asp Val Ile Ala Asn Gly Val Ser Gly Asp
         305                 310                 315
```

```
ATT ACC TCG AGG CCA TTG GAG TAT GTT GCT CGA AGG GTG CGA GCA GCC      1067
Ile Thr Ser Arg Pro Leu Glu Tyr Val Ala Arg Arg Val Arg Ala Ala
    320                 325                 330

ATT AAA ATG GTG ACG AGT GAT TAC GCA AAC TCG ACG ATT GAT TTC TTA      1115
Ile Lys Met Val Thr Ser Asp Tyr Ala Asn Ser Thr Ile Asp Phe Leu
335                 340                 345                 350

AAA AAC CAG GAG GAT TTG TCA AAA TAT CAA GAT ATT CAT GCA TTT AGA      1163
Lys Asn Gln Glu Asp Leu Ser Lys Tyr Gln Asp Ile His Ala Phe Arg
                    355                 360                 365

AGC AAG GAA GGT CCT TTT TAT GGA AAC CCT AAT CTT GGG GTT ATA AGT      1211
Ser Lys Glu Gly Pro Phe Tyr Gly Asn Pro Asn Leu Gly Val Ile Ser
                370                 375                 380

TGG ATA AGT TTG CCA TTA TTA GGA TTG GAT TTT GGG TGG GGA AAA GAG      1259
Trp Ile Ser Leu Pro Leu Leu Gly Leu Asp Phe Gly Trp Gly Lys Glu
            385                 390                 395

ATA CAT ATG AGC CCT GGA ACT CAT GAA TAT GAT GGT GAT TGT GTG ATA      1307
Ile His Met Ser Pro Gly Thr His Glu Tyr Asp Gly Asp Cys Val Ile
        400                 405                 410

CTT CCA GGA AAA GAA GGG GAT GGA TCT TTG ACT GTT GCA ATC ATT CTT      1355
Leu Pro Gly Lys Glu Gly Asp Gly Ser Leu Thr Val Ala Ile Ile Leu
415                 420                 425                 430

CAA GCT GTT CAT GTG GAT GCT TTC AAG AAC TTC TTC TAT GAA GAA ATT      1403
Gln Ala Val His Val Asp Ala Phe Lys Asn Phe Phe Tyr Glu Glu Ile
                435                 440                 445

GAA TGT TGAAAAACAT AAGTGTTTTA TGAGAAGAAA GGAAACAAAT TAAGAACATG       1459
Glu Cys

TAGCTTTTCC TAAATTGACA TTGTTAGTCA TGGTCTAAGC AAAATAAACT CTTTATCTAC    1519

ACATTATTTC AATATATTTT CCT                                             1542
```

( 2 ) INFORMATION FOR SEQ ID NO:2:

( i ) SEQUENCE CHARACTERISTICS:
        ( A ) LENGTH: 448 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Val Ser Leu Lys His His Trp Val Val Lys Pro Ala Glu Ala
 1               5                   10                  15

Thr Trp Asn Gly Thr Val Ser Leu Ser Glu Cys Asp Gln Thr Phe Ala
                20                  25                  30

Val Thr His Val Pro Thr Ile Tyr Tyr Arg Phe Cys His Asp Cys
                35                  40                  45

Leu Pro Ser Thr Asp Asn Ile Ile Lys Thr Leu Arg Thr Ser Leu Ser
        50                  55                  60

Lys Ala Leu Val His Phe Tyr Pro Leu Ser Gly Arg Leu Arg Trp Ile
65                  70                  75                  80

Ala Gly Ser Arg Leu Glu Leu Asp Cys Asn Ala Ser Gly Ile Val Leu
                85                  90                  95

Met Glu Ala Glu Thr Glu Ala Lys Leu Asp Asp Leu Gly Asp Phe Ser
                100                 105                 110

Pro Ser Pro Asp Leu Asn Ser Leu Phe Pro Arg Val Asp Tyr Thr Ile
            115                 120                 125

Pro Ile Asp Glu Leu Pro Leu Leu Phe Val Gln Leu Thr Lys Phe Gln
        130                 135                 140

Cys Gly Gly Ile Ala Leu Ser Phe Ala Ile Ser His Ala Val Val Asp
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Gly | Gln | Ser | Ala | Leu | Tyr | Phe | Leu | Thr | Glu | Trp | Ala | Ser | Leu | Ala | Arg |
|     |     |     |     | 165 |     |     |     |     | 170 |     |     |     |     | 175 |     |
| Gly | Glu | Pro | Leu | Gly | Asn | Glu | Pro | Phe | His | Asp | Arg | Lys | Phe | Leu | Arg |
|     |     |     | 180 |     |     |     |     | 185 |     |     |     |     | 190 |     |     |
| Ala | Gly | Glu | Pro | Pro | Ile | Ala | Tyr | Pro | Thr | Phe | Glu | His | Leu | Gln | Phe |
|     |     | 195 |     |     |     |     | 200 |     |     |     |     | 205 |     |     |     |
| Asn | Pro | Pro | Pro | Leu | Leu | Leu | Gly | Gln | Ser | Ser | Ser | Glu | Glu | Glu | Lys |
|     | 210 |     |     |     |     | 215 |     |     |     |     | 220 |     |     |     |     |
| Lys | Asn | Glu | Thr | Lys | Gly | Ser | Met | Leu | Lys | Leu | Thr | Lys | His | Gln | Val |
| 225 |     |     |     |     | 230 |     |     |     |     | 235 |     |     |     |     | 240 |
| Glu | Met | Leu | Arg | Lys | Lys | Ala | Asn | Gln | Gly | Asn | Gln | Gly | Arg | Ser | Tyr |
|     |     |     |     | 245 |     |     |     |     | 250 |     |     |     |     | 255 |     |
| Thr | Arg | Tyr | Glu | Val | Val | Thr | Ala | His | Ile | Trp | Arg | Cys | Ala | Cys | Lys |
|     |     |     | 260 |     |     |     |     | 265 |     |     |     |     | 270 |     |     |
| Ala | Arg | Gly | His | Lys | Phe | Glu | Gln | Pro | Thr | Asn | Leu | Cys | Ile | Cys | Val |
|     |     | 275 |     |     |     |     | 280 |     |     |     |     | 285 |     |     |     |
| Asn | Ile | Arg | Asn | Ile | Met | Gln | Pro | Pro | Leu | Pro | Lys | Ser | Tyr | Phe | Gly |
|     | 290 |     |     |     |     | 295 |     |     |     |     | 300 |     |     |     |     |
| Asn | Ala | Ile | Val | Asp | Val | Ile | Ala | Asn | Gly | Val | Ser | Gly | Asp | Ile | Thr |
| 305 |     |     |     |     | 310 |     |     |     |     | 315 |     |     |     |     | 320 |
| Ser | Arg | Pro | Leu | Glu | Tyr | Val | Ala | Arg | Arg | Val | Arg | Ala | Ala | Ile | Lys |
|     |     |     |     | 325 |     |     |     |     | 330 |     |     |     |     | 335 |     |
| Met | Val | Thr | Ser | Asp | Tyr | Ala | Asn | Ser | Thr | Ile | Asp | Phe | Leu | Lys | Asn |
|     |     |     | 340 |     |     |     |     | 345 |     |     |     |     | 350 |     |     |
| Gln | Glu | Asp | Leu | Ser | Lys | Tyr | Gln | Asp | Ile | His | Ala | Phe | Arg | Ser | Lys |
|     |     | 355 |     |     |     |     | 360 |     |     |     |     | 365 |     |     |     |
| Glu | Gly | Pro | Phe | Tyr | Gly | Asn | Pro | Asn | Leu | Gly | Val | Ile | Ser | Trp | Ile |
|     | 370 |     |     |     |     | 375 |     |     |     |     | 380 |     |     |     |     |
| Ser | Leu | Pro | Leu | Leu | Gly | Leu | Asp | Phe | Gly | Trp | Gly | Lys | Glu | Ile | His |
| 385 |     |     |     |     | 390 |     |     |     |     | 395 |     |     |     |     | 400 |
| Met | Ser | Pro | Gly | Thr | His | Glu | Tyr | Asp | Gly | Asp | Cys | Val | Ile | Leu | Pro |
|     |     |     | 405 |     |     |     |     | 410 |     |     |     |     | 415 |     |     |
| Gly | Lys | Glu | Gly | Asp | Gly | Ser | Leu | Thr | Val | Ala | Ile | Ile | Leu | Gln | Ala |
|     |     |     | 420 |     |     |     |     | 425 |     |     |     |     | 430 |     |     |
| Val | His | Val | Asp | Ala | Phe | Lys | Asn | Phe | Phe | Tyr | Glu | Glu | Ile | Glu | Cys |
|     |     | 435 |     |     |     |     | 440 |     |     |     |     | 445 |     |     |     |

( 2 ) INFORMATION FOR SEQ ID NO:3:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Nicotiana tabacum
        ( C ) INDIVIDUAL ISOLATE: Ant43D ( i x ) FEATURE:
        ( A ) NAME/KEY: CDS
        ( B ) LOCATION: 41..397

( x i ) SEQUENCE DESCRIPTION: SEQ ID NO:3:

| | | | | | | | | | | | | | | | |
|---|---|---|---|---|---|---|---|---|---|---|---|---|---|---|---|
| CTTACATTTC | TTCAATAGTT | TAGTCCATAA | AGCAATAGAT | ATG | GCT | CGG | TTT | CTT | | | | | | | 55 |
| | | | | Met | Ala | Arg | Phe | Leu | | | | | | | |
| | | | | 1 | | | | 5 | | | | | | | |

| GTG | TTC | CTT | GCT | TTA | GCC | CTT | GTA | ATA | ATT | TCA | AAG | AAG | GGC | GCG | TTG | 103 |
|---|---|---|---|---|---|---|---|---|---|---|---|---|---|---|---|---|
| Val | Phe | Leu | Ala | Leu | Ala | Leu | Val | Ile | Ile | Ser | Lys | Lys | Gly | Ala | Leu | |
| | | | | 10 | | | | | 15 | | | | | 20 | | |

| GGT | GCT | CCT | CCT | TCC | TGT | CCA | ACA | GTT | ACA | ACG | CAG | CTG | GCT | CCT | TGT | 151 |
|---|---|---|---|---|---|---|---|---|---|---|---|---|---|---|---|---|
| Gly | Ala | Pro | Pro | Ser | Cys | Pro | Thr | Val | Thr | Thr | Gln | Leu | Ala | Pro | Cys | |
| | | | 25 | | | | | 30 | | | | | | 35 | | |

| CTA | TCG | TAC | ATT | CAA | GGT | GGA | GGT | GAT | CCA | TCT | GTA | CCT | TGC | TGC | ACT | 199 |
|---|---|---|---|---|---|---|---|---|---|---|---|---|---|---|---|---|
| Leu | Ser | Tyr | Ile | Gln | Gly | Gly | Gly | Asp | Pro | Ser | Val | Pro | Cys | Cys | Thr | |
| | | 40 | | | | | 45 | | | | | 50 | | | | |

| GGT | ATA | AAT | AAC | ATA | TAT | GAA | CTT | GCT | AAA | ACC | AAA | GAA | GAC | CGA | GTC | 247 |
|---|---|---|---|---|---|---|---|---|---|---|---|---|---|---|---|---|
| Gly | Ile | Asn | Asn | Ile | Tyr | Glu | Leu | Ala | Lys | Thr | Lys | Glu | Asp | Arg | Val | |
| | 55 | | | | | 60 | | | | | 65 | | | | | |

| GCT | ATC | TGC | AAC | TGC | TTA | AAA | ACC | GCA | TTT | ACT | CAT | GCT | GGA | AAT | GTC | 295 |
|---|---|---|---|---|---|---|---|---|---|---|---|---|---|---|---|---|
| Ala | Ile | Cys | Asn | Cys | Leu | Lys | Thr | Ala | Phe | Thr | His | Ala | Gly | Asn | Val | |
| 70 | | | | | 75 | | | | | 80 | | | | | 85 | |

| AAT | CCC | ACT | CTC | GTA | GCT | CAA | CTC | CCC | AAG | AAA | TGT | GGC | ATT | TCT | TTT | 343 |
|---|---|---|---|---|---|---|---|---|---|---|---|---|---|---|---|---|
| Asn | Pro | Thr | Leu | Val | Ala | Gln | Leu | Pro | Lys | Lys | Cys | Gly | Ile | Ser | Phe | |
| | | | | 90 | | | | | 95 | | | | | 100 | | |

| AAT | ATG | CCT | CCT | ATT | GAT | AAA | AAC | TAC | GAC | TGT | AAC | ACG | ATT | TCT | ATG | 391 |
|---|---|---|---|---|---|---|---|---|---|---|---|---|---|---|---|---|
| Asn | Met | Pro | Pro | Ile | Asp | Lys | Asn | Tyr | Asp | Cys | Asn | Thr | Ile | Ser | Met | |
| | | | 105 | | | | | 110 | | | | | 115 | | | |

| | | | | | |
|---|---|---|---|---|---|
| TAC | TGATGAATGG | GTAGTGAATC | TCGGAAGCTG | CTCAAATTTA | TGAATAAAAC | 444 |
| Tyr | | | | | | |

ATATATAGAT GTTCATCTCA TGTCTGAAAT CTGAAAGCAA TTTGATCCAC TGTAAACTTC         504

AAATGTATGC AGACGGTTAA ATGTTGAATT ATGATATATA TAAATTTG                     552

( 2 ) INFORMATION FOR SEQ ID NO:4:

( i ) SEQUENCE CHARACTERISTICS:
           ( A ) LENGTH: 118 amino acids
           ( B ) TYPE: amino acid
           ( D ) TOPOLOGY: linear ( i i ) MOLECULE TYPE: protein ( x i ) SEQUENCE DESCRIPTION: SEQ ID NO:4:

| Met | Ala | Arg | Phe | Leu | Val | Phe | Leu | Ala | Leu | Ala | Leu | Val | Ile | Ile | Ser |
|---|---|---|---|---|---|---|---|---|---|---|---|---|---|---|---|
| 1 | | | | 5 | | | | | 10 | | | | | 15 | |

| Lys | Lys | Gly | Ala | Leu | Gly | Ala | Pro | Pro | Ser | Cys | Pro | Thr | Val | Thr | Thr |
|---|---|---|---|---|---|---|---|---|---|---|---|---|---|---|---|
| | | | 20 | | | | 25 | | | | 30 | | | | |

| Gln | Leu | Ala | Pro | Cys | Leu | Ser | Tyr | Ile | Gln | Gly | Gly | Gly | Asp | Pro | Ser |
|---|---|---|---|---|---|---|---|---|---|---|---|---|---|---|---|
| | | 35 | | | | 40 | | | | 45 | | | | | |

| Val | Pro | Cys | Cys | Thr | Gly | Ile | Asn | Asn | Ile | Tyr | Glu | Leu | Ala | Lys | Thr |
|---|---|---|---|---|---|---|---|---|---|---|---|---|---|---|---|
| | 50 | | | | 55 | | | | 60 | | | | | | |

| Lys | Glu | Asp | Arg | Val | Ala | Ile | Cys | Asn | Cys | Leu | Lys | Thr | Ala | Phe | Thr |
|---|---|---|---|---|---|---|---|---|---|---|---|---|---|---|---|
| 65 | | | | 70 | | | | 75 | | | | | 80 | | |

| His | Ala | Gly | Asn | Val | Asn | Pro | Thr | Leu | Val | Ala | Gln | Leu | Pro | Lys | Lys |
|---|---|---|---|---|---|---|---|---|---|---|---|---|---|---|---|
| | | | 85 | | | | 90 | | | | 95 | | | | |

| Cys | Gly | Ile | Ser | Phe | Asn | Met | Pro | Pro | Ile | Asp | Lys | Asn | Tyr | Asp | Cys |
|---|---|---|---|---|---|---|---|---|---|---|---|---|---|---|---|
| | | | 100 | | | | 105 | | | | 110 | | | | |

| Asn | Thr | Ile | Ser | Met | Tyr |
|---|---|---|---|---|---|
| | | 115 | | | |

( 2 ) INFORMATION FOR SEQ ID NO:5:

( i ) SEQUENCE CHARACTERISTICS:
    ( A ) LENGTH: 612 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Nicotiana tabacum
    ( C ) INDIVIDUAL ISOLATE: Ant9

( i x ) FEATURE:
    ( A ) NAME/KEY: CDS
    ( B ) LOCATION: 344..442

( x i ) SEQUENCE DESCRIPTION: SEQ ID NO:5:

| | | | | | |
|---|---|---|---|---|---|
| TGTCAGAGAG | GGTGATGTTT | TAACATTGTT | AGAGTCTGAC | AGGTCCCTTG | ACATTTCTCA | 60 |
| TGATAAACCT | GTTCTGGTCA | TCATGAGAAA | TGTCTAGCCT | CTCTCTCAGA | CTCTAACAAT | 120 |
| GTTAAAACAT | CACCCTCTCT | GACAGGTCCC | TTGACATTTC | TCATGATAAA | CCTGTTCTGG | 180 |
| TCATCAAGAA | ACTTGACTCT | CACCTGAGTT | ACCTGTCCTC | TGGACCCAGT | ACGGCCCATG | 240 |
| ACTTTCACCA | CAATAGCATG | CTTGGTCGCA | GATTCCATCC | TTGAGAGGAG | CAGACGAGCG | 300 |
| AGCACAAAGC | GCAAATTGCT | ATGACGGCCG | AATAGGAGAA | AAA ATG CCT | TCC CTC | 355 |
|  |  |  |  | Met Pro | Ser Leu |  |
|  |  |  |  | 1 |  |  |

TCA GTG CAA TCT TCC TCC CCT CTC TTG TGC GGC AAA CTG AGT TTG ATG   403
Ser Val Gln Ser Ser Ser Pro Leu Leu Cys Gly Lys Leu Ser Leu Met
 5              10              15              20

GGG TCC GTG CCT ACC AGT TCC CAG TCA CTG GGC GAA TAATATCATA        449
Gly Ser Val Pro Thr Ser Ser Gln Ser Leu Gly Glu
            25              30

| | | | | | |
|---|---|---|---|---|---|
| GTTCTAAAAT | CAATAAATTT | ACTTTGTCCC | TTCTATCTTT | TTTTCTTCT | TTTTCATTGG | 509 |
| TGCTCTTTAT | GCTAATGTCC | TCACTCCTCT | GTTCTATCAC | AGAGCAAGGT | CAGGAAAGAG | 569 |
| TTTGTATTGT | CATATGAAAT | CAATAAAACA | AACTGTTTAC | CCG |  | 612 |

( 2 ) INFORMATION FOR SEQ ID NO:6:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

Met Pro Ser Leu Ser Val Gln Ser Ser Ser Pro Leu Leu Cys Gly Lys
 1               5              10              15

Leu Ser Leu Met Gly Ser Val Pro Thr Ser Ser Gln Ser Leu Gly Glu
            20              25              30

( 2 ) INFORMATION FOR SEQ ID NO:7:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Nicotiana tabacum
    ( C ) INDIVIDUAL ISOLATE: Ant52

( i x ) FEATURE:
    ( A ) NAME/KEY: CDS
    ( B ) LOCATION: 3..95

( x i ) SEQUENCE DESCRIPTION: SEQ ID NO:7:

```
CC  CAT  AAC  TGC  CTT  AAT  TGC  AAT  TCT  AAA  AGG  CAA  CAA  GAT  TCT  TAC        47
    His  Asn  Cys  Leu  Asn  Cys  Asn  Ser  Lys  Arg  Gln  Gln  Asp  Ser  Tyr
     1              5                        10                        15

TTC  TTC  ACT  GAT  CCA  ATG  AAA  GCA  CAA  TCA  ATA  GTA  GGA  ACT  GTC  ACC        95
Phe  Phe  Thr  Asp  Pro  Met  Lys  Ala  Gln  Ser  Ile  Val  Gly  Thr  Val  Thr
                   20                        25                        30

C                                                                                      96
```

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
His  Asn  Cys  Leu  Asn  Cys  Asn  Ser  Lys  Arg  Gln  Gln  Asp  Ser  Tyr  Phe
 1              5                        10                        15

Phe  Thr  Asp  Pro  Met  Lys  Ala  Gln  Ser  Ile  Val  Gly  Thr  Val  Thr
              20                        25                        30
```

( 2 ) INFORMATION FOR SEQ ID NO:9:

( i ) SEQUENCE CHARACTERISTICS:
        ( A ) LENGTH: 1201 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Nicotiana tabacum
        ( C ) INDIVIDUAL ISOLATE: Ant59

( i x ) FEATURE:
        ( A ) NAME/KEY: CDS
        ( B ) LOCATION: 1..1119

( x i ) SEQUENCE DESCRIPTION: SEQ ID NO:9:

```
ATC  TTT  AGT  AGC  CAA  ATA  TGG  ACT  CAA  CCT  AAT  TCT  GAA  ATG  AAT  AAT        48
Ile  Phe  Ser  Ser  Gln  Ile  Trp  Thr  Gln  Pro  Asn  Ser  Glu  Met  Asn  Asn
 1              5                        10                        15

GAT  CTT  GTG  ATC  CCC  GCC  ATT  TTC  AAC  CAT  GAG  AAG  CTT  AGG  ACC  ATT        96
Asp  Leu  Val  Ile  Pro  Ala  Ile  Phe  Asn  His  Glu  Lys  Leu  Arg  Thr  Ile
              20                        25                        30

TCA  CGT  GAA  TGC  GAT  CCC  AAG  CGT  AAA  CTA  GCC  GAA  AGC  AAT  TCA  GGA       144
Ser  Arg  Glu  Cys  Asp  Pro  Lys  Arg  Lys  Leu  Ala  Glu  Ser  Asn  Ser  Gly
              35                        40                        45
```

| | | | | | | | | | | | | | | | | |
|---|---|---|---|---|---|---|---|---|---|---|---|---|---|---|---|---|
| GAC | ATC | ATG | GGA | GAA | GTT | AAG | AAG | ACT | CAT | CAA | GCT | ATT | CAA | TCA | CTT | 192 |
| Asp | Ile | Met | Gly | Glu | Val | Lys | Lys | Thr | His | Gln | Ala | Ile | Gln | Ser | Leu | |
| | | 50 | | | | 55 | | | | | 60 | | | | | |
| GAT | AAA | AGT | ATG | TCA | ACA | TTG | GAG | AAT | GAA | TTG | GCA | ATA | GCT | CGG | ACA | 240 |
| Asp | Lys | Ser | Met | Ser | Thr | Leu | Glu | Asn | Glu | Leu | Ala | Ile | Ala | Arg | Thr | |
| 65 | | | | | 70 | | | | | 75 | | | | | 80 | |
| AGG | CAA | ACA | ATC | AGT | CAC | AAT | GCA | AAG | GAA | AAT | AGG | GCT | TCA | AAT | CAC | 288 |
| Arg | Gln | Thr | Ile | Ser | His | Asn | Ala | Lys | Glu | Asn | Arg | Ala | Ser | Asn | His | |
| | | | | 85 | | | | | 90 | | | | | 95 | | |
| ACC | ACA | CCG | AAT | AAA | GCA | TTC | ATC | GTG | GTG | GGA | ATT | AAT | ACC | GCA | TTC | 336 |
| Thr | Thr | Pro | Asn | Lys | Ala | Phe | Ile | Val | Val | Gly | Ile | Asn | Thr | Ala | Phe | |
| | | | 100 | | | | | 105 | | | | | 110 | | | |
| AGC | AGC | AGA | AAA | AGA | CGC | GAT | TCT | CTT | AGA | GAA | ACT | TGG | ATG | CCT | AAA | 384 |
| Ser | Ser | Arg | Lys | Arg | Arg | Asp | Ser | Leu | Arg | Glu | Thr | Trp | Met | Pro | Lys | |
| | | 115 | | | | | 120 | | | | | 125 | | | | |
| GGG | GAT | AAG | CTA | AGG | AAG | CTA | GAG | AAA | GAG | AAG | GGA | ATC | GTG | ATA | CGG | 432 |
| Gly | Asp | Lys | Leu | Arg | Lys | Leu | Glu | Lys | Glu | Lys | Gly | Ile | Val | Ile | Arg | |
| | 130 | | | | | 135 | | | | | 140 | | | | | |
| TTT | GTG | ATA | GGA | CAC | AGT | GCT | ACA | CGA | GGA | GGA | GTT | CTT | GAT | CGT | GCC | 480 |
| Phe | Val | Ile | Gly | His | Ser | Ala | Thr | Arg | Gly | Gly | Val | Leu | Asp | Arg | Ala | |
| 145 | | | | | 150 | | | | | 155 | | | | | 160 | |
| ATT | GAT | AGT | GAG | GAT | GCT | CAG | TAC | AAG | GAT | TTC | CTT | CGA | CTT | GAC | CAC | 528 |
| Ile | Asp | Ser | Glu | Asp | Ala | Gln | Tyr | Lys | Asp | Phe | Leu | Arg | Leu | Asp | His | |
| | | | | 165 | | | | | 170 | | | | | 175 | | |
| GTT | GAG | GGT | TAT | CAT | GAG | CTG | TCC | ACC | AAG | ACA | AGA | TTG | TAT | TTC | TCT | 576 |
| Val | Glu | Gly | Tyr | His | Glu | Leu | Ser | Thr | Lys | Thr | Arg | Leu | Tyr | Phe | Ser | |
| | | | 180 | | | | | 185 | | | | | 190 | | | |
| AAA | GCT | GTC | TCC | ATT | TGG | GAC | GCT | GAC | TTC | TAC | GTT | AAA | GTG | GAC | GAT | 624 |
| Lys | Ala | Val | Ser | Ile | Trp | Asp | Ala | Asp | Phe | Tyr | Val | Lys | Val | Asp | Asp | |
| | | 195 | | | | | 200 | | | | | 205 | | | | |
| GAT | GTC | CAT | CTC | AAC | TTA | GGT | ATG | CTT | GCG | AAC | ACA | TTA | GCA | AAA | TAC | 672 |
| Asp | Val | His | Leu | Asn | Leu | Gly | Met | Leu | Ala | Asn | Thr | Leu | Ala | Lys | Tyr | |
| | 210 | | | | | 215 | | | | | 220 | | | | | |
| AAA | TCC | AAA | CCA | AGA | GTC | TAC | ATT | GGA | TGC | ATG | AAA | TCA | GGG | CCA | GTT | 720 |
| Lys | Ser | Lys | Pro | Arg | Val | Tyr | Ile | Gly | Cys | Met | Lys | Ser | Gly | Pro | Val | |
| 225 | | | | | 230 | | | | | 235 | | | | | 240 | |
| CTT | TCC | CAA | AAA | GGA | GTA | AGG | TAT | TAT | GAG | CCC | GAG | TAT | TGG | AAA | TTT | 768 |
| Leu | Ser | Gln | Lys | Gly | Val | Arg | Tyr | Tyr | Glu | Pro | Glu | Tyr | Trp | Lys | Phe | |
| | | | | 245 | | | | | 250 | | | | | 255 | | |
| GGA | GAA | GAA | GGA | AAC | AAG | TAT | TTC | AGG | CAT | GCC | ACG | GGT | CAA | ATA | TAT | 816 |
| Gly | Glu | Glu | Gly | Asn | Lys | Tyr | Phe | Arg | His | Ala | Thr | Gly | Gln | Ile | Tyr | |
| | | | 260 | | | | | 265 | | | | | 270 | | | |
| GGC | ATC | TCT | AGA | GAC | CTT | GCT | TCA | TAT | ATC | TCC | ATC | AAC | TCG | GGA | ATA | 864 |
| Gly | Ile | Ser | Arg | Asp | Leu | Ala | Ser | Tyr | Ile | Ser | Ile | Asn | Ser | Gly | Ile | |
| | | 275 | | | | | 280 | | | | | 285 | | | | |
| TTA | CAT | AGA | TAT | GCA | AAT | GAA | GAC | GTA | TCA | TTG | GGA | TCA | TGG | TTA | ATT | 912 |
| Leu | His | Arg | Tyr | Ala | Asn | Glu | Asp | Val | Ser | Leu | Gly | Ser | Trp | Leu | Ile | |
| | 290 | | | | | 295 | | | | | 300 | | | | | |
| GGG | TTG | GAA | GTA | GAG | CAT | GTG | GAT | GAG | CGT | TCA | ATG | TGC | TGT | GGA | ACA | 960 |
| Gly | Leu | Glu | Val | Glu | His | Val | Asp | Glu | Arg | Ser | Met | Cys | Cys | Gly | Thr | |
| 305 | | | | | 310 | | | | | 315 | | | | | 320 | |
| CCT | CCA | GAT | TGT | GAG | TGG | AAA | GCC | AAA | GGA | GGA | AAT | ATA | TGT | GTG | GCA | 1008 |
| Pro | Pro | Asp | Cys | Glu | Trp | Lys | Ala | Lys | Gly | Gly | Asn | Ile | Cys | Val | Ala | |
| | | | | 325 | | | | | 330 | | | | | 335 | | |
| TCA | TTT | GAT | TGG | TCA | TGC | AGT | GGG | ATA | TGC | AAG | TCG | GTA | GAG | AGG | ATG | 1056 |
| Ser | Phe | Asp | Trp | Ser | Cys | Ser | Gly | Ile | Cys | Lys | Ser | Val | Glu | Arg | Met | |
| | | | 340 | | | | | 345 | | | | | 350 | | | |
| AAA | GAT | GTG | CAC | CAC | TCA | TGC | GGC | GAA | GGT | GAC | GCA | GCT | CTT | TGG | AAT | 1104 |
| Lys | Asp | Val | His | His | Ser | Cys | Gly | Glu | Gly | Asp | Ala | Ala | Leu | Trp | Asn | |

```
                     355                      360                           365
GTT CCT CTC TCA TGAGATTTAT TGGAGAGAAC TTAATTAATT ATCCACATAG                              1156
Val Pro Leu Ser
    370

TATTTCCTTT CGATTAATTA ATAATTTACT TGCGCAATGC AATTC                                        1201
```

( 2 ) INFORMATION FOR SEQ ID NO:10:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ile Phe Ser Ser Gln Ile Trp Thr Gln Pro Asn Ser Glu Met Asn Asn
 1               5                  10                  15

Asp Leu Val Ile Pro Ala Ile Phe Asn His Glu Lys Leu Arg Thr Ile
            20                  25                  30

Ser Arg Glu Cys Asp Pro Lys Arg Lys Leu Ala Glu Ser Asn Ser Gly
        35                  40                  45

Asp Ile Met Gly Glu Val Lys Lys Thr His Gln Ala Ile Gln Ser Leu
    50                  55                  60

Asp Lys Ser Met Ser Thr Leu Glu Asn Glu Leu Ala Ile Ala Arg Thr
65                  70                  75                  80

Arg Gln Thr Ile Ser His Asn Ala Lys Glu Asn Arg Ala Ser Asn His
                85                  90                  95

Thr Thr Pro Asn Lys Ala Phe Ile Val Gly Ile Asn Thr Ala Phe
            100                 105                 110

Ser Ser Arg Lys Arg Arg Asp Ser Leu Arg Glu Thr Trp Met Pro Lys
        115                 120                 125

Gly Asp Lys Leu Arg Lys Leu Glu Lys Glu Lys Gly Ile Val Ile Arg
    130                 135                 140

Phe Val Ile Gly His Ser Ala Thr Arg Gly Gly Val Leu Asp Arg Ala
145                 150                 155                 160

Ile Asp Ser Glu Asp Ala Gln Tyr Lys Asp Phe Leu Arg Leu Asp His
                165                 170                 175

Val Glu Gly Tyr His Glu Leu Ser Thr Lys Thr Arg Leu Tyr Phe Ser
            180                 185                 190

Lys Ala Val Ser Ile Trp Asp Ala Asp Phe Tyr Val Lys Val Asp Asp
        195                 200                 205

Asp Val His Leu Asn Leu Gly Met Leu Ala Asn Thr Leu Ala Lys Tyr
    210                 215                 220

Lys Ser Lys Pro Arg Val Tyr Ile Gly Cys Met Lys Ser Gly Pro Val
225                 230                 235                 240

Leu Ser Gln Lys Gly Val Arg Tyr Tyr Glu Pro Glu Tyr Trp Lys Phe
                245                 250                 255

Gly Glu Glu Gly Asn Lys Tyr Phe Arg His Ala Thr Gly Gln Ile Tyr
            260                 265                 270

Gly Ile Ser Arg Asp Leu Ala Ser Tyr Ile Ser Ile Asn Ser Gly Ile
        275                 280                 285

Leu His Arg Tyr Ala Asn Glu Asp Val Ser Leu Gly Ser Trp Leu Ile
    290                 295                 300

Gly Leu Glu Val Glu His Val Asp Glu Arg Ser Met Cys Cys Gly Thr
305                 310                 315                 320
```

| | | | | | | | | | | | | | | | |
|---|---|---|---|---|---|---|---|---|---|---|---|---|---|---|---|
| Pro | Pro | Asp | Cys | Glu<br>325 | Trp | Lys | Ala | Lys | Gly<br>330 | Gly | Asn | Ile | Cys | Val<br>335 | Ala |
| Ser | Phe | Asp | Trp<br>340 | Ser | Cys | Ser | Gly | Ile<br>345 | Cys | Lys | Ser | Val | Glu<br>350 | Arg | Met |
| Lys | Asp | Val<br>355 | His | His | Ser | Cys | Gly<br>360 | Glu | Gly | Asp | Ala | Ala<br>365 | Leu | Trp | Asn |
| Val | Pro<br>370 | Leu | Ser | | | | | | | | | | | | |

( 2 ) INFORMATION FOR SEQ ID NO:11:

( i ) SEQUENCE CHARACTERISTICS:
        ( A ) LENGTH: 952 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Nicotiana tabacum
        ( C ) INDIVIDUAL ISOLATE: Ant66

( i x ) FEATURE:
        ( A ) NAME/KEY: CDS
        ( B ) LOCATION: 1..711

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| ATC<br>Ile<br>1 | ATG<br>Met | ACC<br>Thr | ATC<br>Ile | TCT<br>Ser<br>5 | AAG<br>Lys | GAC<br>Asp | AGG<br>Arg | GTG<br>Val | AAG<br>Lys<br>10 | CCA<br>Pro | TCC<br>Ser | CCT<br>Pro | CTG<br>Leu | CCC<br>Pro<br>15 | GAC<br>Asp | 48 |
| TCG<br>Ser | TGG<br>Trp | AAG<br>Lys | CTC<br>Leu<br>20 | AAC<br>Asn | GAA<br>Glu | ATC<br>Ile | TTT<br>Phe | GCC<br>Ala<br>25 | ACT<br>Thr | GGA<br>Gly | ATC<br>Ile | GTC<br>Val | CTC<br>Leu<br>30 | GGA<br>Gly | ACC<br>Thr | 96 |
| TAT<br>Tyr | CAA<br>Gln | GCT<br>Ala<br>35 | ATT<br>Ile | ATG<br>Met | ACT<br>Thr | GTG<br>Val | GTG<br>Val<br>40 | TTC<br>Phe | TTC<br>Phe | TAT<br>Tyr | CTT<br>Leu | GCA<br>Ala<br>45 | GCT<br>Ala | GAC<br>Asp | ACT<br>Thr | 144 |
| GAC<br>Asp | TTC<br>Phe<br>50 | TTT<br>Phe | ACA<br>Thr | GAG<br>Glu | AAA<br>Lys | TTC<br>Phe<br>55 | AAC<br>Asn | GTT<br>Val | AAA<br>Lys | TCA<br>Ser | ATC<br>Ile<br>60 | AGG<br>Arg | GAT<br>Asp | AAT<br>Asn | CCC<br>Pro | 192 |
| TAC<br>Tyr<br>65 | GAG<br>Glu | CTT<br>Leu | ACA<br>Thr | GCT<br>Ala | GCT<br>Ala<br>70 | GTA<br>Val | TAC<br>Tyr | CTT<br>Leu | CAA<br>Gln | GTG<br>Val<br>75 | AGC<br>Ser | ATC<br>Ile | ATC<br>Ile | AGC<br>Ser | CAA<br>Gln<br>80 | 240 |
| GCT<br>Ala | CTT<br>Leu | ATC<br>Ile | TTT<br>Phe | GTG<br>Val<br>85 | ACA<br>Thr | AGA<br>Arg | TCA<br>Ser | AGA<br>Arg | AGC<br>Ser<br>90 | TGG<br>Trp | TCA<br>Ser | TTT<br>Phe | TTG<br>Leu | GAA<br>Glu<br>95 | CGC<br>Arg | 288 |
| CCG<br>Pro | GGT<br>Gly | TTC<br>Phe | TTG<br>Leu<br>100 | CTT<br>Leu | GTC<br>Val | ACT<br>Thr | GCT<br>Ala | TTC<br>Phe<br>105 | CTC<br>Leu | TTA<br>Leu | GCC<br>Ala | CAA<br>Gln | TTT<br>Phe<br>110 | GTG<br>Val | GCT<br>Ala | 336 |
| ACA<br>Thr | TTA<br>Leu | ATC<br>Ile<br>115 | GCT<br>Ala | GTC<br>Val | TAC<br>Tyr | GCC<br>Ala | AAC<br>Asn<br>120 | TGG<br>Trp | AAG<br>Lys | TTT<br>Phe | GCT<br>Ala | AGG<br>Arg<br>125 | ATC<br>Ile | CAT<br>His | GGA<br>Gly | 384 |
| ATT<br>Ile | GGT<br>Gly<br>130 | TGG<br>Trp | GGA<br>Gly | TGG<br>Trp | GCA<br>Ala | GGA<br>Gly<br>135 | ATC<br>Ile | ATC<br>Ile | TGG<br>Trp | ATC<br>Ile | TAC<br>Tyr<br>140 | ACA<br>Thr | ATT<br>Ile | ATC<br>Ile | ACC<br>Thr | 432 |
| TAT<br>Tyr<br>145 | ATC<br>Ile | CCT<br>Pro | CTT<br>Leu | GAT<br>Asp | ATT<br>Ile<br>150 | CTC<br>Leu | AAA<br>Lys | TTC<br>Phe | ATC<br>Ile | AGT<br>Ser<br>155 | CGT<br>Arg | TAC<br>Tyr | ACG<br>Thr | TTG<br>Leu | AGT<br>Ser<br>160 | 480 |
| GGT<br>Gly | GAG<br>Glu | GCC<br>Ala | TGG<br>Trp | AAT<br>Asn | TCA<br>Ser | ATG<br>Met | ATC<br>Ile | CAA<br>Gln | AAT<br>Asn | AAG<br>Lys | ACT<br>Thr | GCT<br>Ala | TTC<br>Phe | ACA<br>Thr | ACC<br>Thr | 528 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Gly | Glu | Ala | Trp | Asn<br>165 | Ser | Met | Ile | Gln | Asn<br>170 | Lys | Thr | Ala | Phe | Thr<br>175 | Thr | |

| AAG | AAG | GAT | TAT | GGA | AAA | GGT | GAG | AGG | GAA | GCA | CAA | TGG | GCT | GTG | GCG | 576 |
|-----|-----|-----|-----|-----|-----|-----|-----|-----|-----|-----|-----|-----|-----|-----|-----|-----|
| Lys | Lys | Asp | Tyr<br>180 | Gly | Lys | Gly | Glu | Arg<br>185 | Glu | Ala | Gln | Trp | Ala<br>190 | Val | Ala | |

| CAA | CGA | ACA | CTA | CAC | GGT | CTC | CAG | ACT | GCT | GAA | AGC | AAT | GGC | CTA | TTC | 624 |
|-----|-----|-----|-----|-----|-----|-----|-----|-----|-----|-----|-----|-----|-----|-----|-----|-----|
| Gln | Arg | Thr<br>195 | Leu | His | Gly | Leu | Gln<br>200 | Thr | Ala | Glu | Ser | Asn<br>205 | Gly | Leu | Phe | |

| CAT | GAC | AAG | AAC | TAC | AGA | GAA | TTG | AAT | GAG | ATT | GCT | GAA | CAG | GCT | AAA | 672 |
|-----|-----|-----|-----|-----|-----|-----|-----|-----|-----|-----|-----|-----|-----|-----|-----|-----|
| His | Asp<br>210 | Lys | Asn | Tyr | Arg | Glu<br>215 | Leu | Asn | Glu | Ile | Ala<br>220 | Glu | Gln | Ala | Lys | |

| CGT | CGC | GCT | GAA | GTT | GCA | AAA | TAT | ACA | CAT | GAG | CCA | TGAAATAAC |     |     |     | 718 |
|-----|-----|-----|-----|-----|-----|-----|-----|-----|-----|-----|-----|-----------|-----|-----|-----|-----|
| Arg<br>225 | Arg | Ala | Glu | Val | Ala<br>230 | Lys | Tyr | Thr | His | Glu<br>235 | Pro | | | | | |

```
TTGATTATCT CAATAACCAT GTTGCAAGAT AGGGGAATAT TAGACTCTCA AGGGACATGT   778

TAAATCTATG TAGTCTAAGT TAAAGGGCAT TTTTGCAGCT ATTTATCAAG AATGTATCTC   838

AATGTTGGAT GAAATCCAAT ATTGGTGAAC TACAAAGGCT AGCTGCTAAT CAAAACTATT   898

AAACTAGTAG TTATATACAT AAAGAAAATT TACTATAGCA AAAAAAAAA AAAA          952
```

( 2 ) INFORMATION FOR SEQ ID NO:12:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Ile<br>1 | Met | Thr | Ile | Ser<br>5 | Lys | Asp | Arg | Val | Lys<br>10 | Pro | Ser | Pro | Leu | Pro<br>15 | Asp |
|---|---|---|---|---|---|---|---|---|---|---|---|---|---|---|---|
| Ser | Trp | Lys | Leu<br>20 | Asn | Glu | Ile | Phe | Ala<br>25 | Thr | Gly | Ile | Val | Leu<br>30 | Gly | Thr |
| Tyr | Gln | Ala<br>35 | Ile | Met | Thr | Val | Val<br>40 | Phe | Phe | Tyr | Leu | Ala<br>45 | Ala | Asp | Thr |
| Asp | Phe<br>50 | Phe | Thr | Glu | Lys | Phe<br>55 | Asn | Val | Lys | Ser | Ile<br>60 | Arg | Asp | Asn | Pro |
| Tyr<br>65 | Glu | Leu | Thr | Ala | Ala<br>70 | Val | Tyr | Leu | Gln | Val<br>75 | Ser | Ile | Ile | Ser | Gln<br>80 |
| Ala | Leu | Ile | Phe | Val<br>85 | Thr | Arg | Ser | Arg | Ser<br>90 | Trp | Ser | Phe | Leu | Glu<br>95 | Arg |
| Pro | Gly | Phe | Leu<br>100 | Leu | Val | Thr | Ala | Phe<br>105 | Leu | Leu | Ala | Gln | Phe<br>110 | Val | Ala |
| Thr | Leu | Ile<br>115 | Ala | Val | Tyr | Ala | Asn<br>120 | Trp | Lys | Phe | Ala | Arg<br>125 | Ile | His | Gly |
| Ile | Gly<br>130 | Trp | Gly | Trp | Ala | Gly<br>135 | Ile | Ile | Trp | Ile | Tyr<br>140 | Thr | Ile | Ile | Thr |
| Tyr<br>145 | Ile | Pro | Leu | Asp | Ile<br>150 | Leu | Lys | Phe | Ile | Ser<br>155 | Arg | Tyr | Thr | Leu | Ser<br>160 |
| Gly | Glu | Ala | Trp | Asn<br>165 | Ser | Met | Ile | Gln | Asn<br>170 | Lys | Thr | Ala | Phe | Thr<br>175 | Thr |
| Lys | Lys | Asp | Tyr<br>180 | Gly | Lys | Gly | Glu | Arg<br>185 | Glu | Ala | Gln | Trp | Ala<br>190 | Val | Ala |
| Gln | Arg | Thr<br>195 | Leu | His | Gly | Leu | Gln<br>200 | Thr | Ala | Glu | Ser | Asn<br>205 | Gly | Leu | Phe |
| His | Asp | Lys | Asn | Tyr | Arg | Glu | Leu | Asn | Glu | Ile | Ala | Glu | Gln | Ala | Lys |

```
                    210                         215                         220
Arg  Arg  Ala  Glu  Val  Ala  Lys  Tyr  Thr  His  Glu  Pro
225                      230                         235
```

( 2 ) INFORMATION FOR SEQ ID NO:13:

( i ) SEQUENCE CHARACTERISTICS:
        ( A ) LENGTH: 305 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Nicotiana tabacum
        ( C ) INDIVIDUAL ISOLATE: Ant67

( x i ) SEQUENCE DESCRIPTION: SEQ ID NO:13:

```
ATTAAACTCT   TGTTGTGTTT   CCCTAGATTC   CCAAGTTCTT   TTTAGCTCCA   TGCTTCTTGT        60

CCTCATGGCA   TCCTGCTCTC   TGTAAAAATT   GAATCTTTTT   ATGTTTTACT   TCCATTCTTG       120

AATTTCATCC   CTTTTGTTTG   CTTCAATTGT   TGCTTCTACC   TTAATCATTT   ATGTATTCCA       180

TGTTGTGGGT   TTTGCTTCTT   CATTTTAAGT   TTAACTCCTG   TGCCCTAAGA   TAATTTTTT        240

TAATGTTTTT   CTTCCATTCT   TGATTTTCTT   TTTCTGTGCA   TTAGGCCTTT   TTGTATATTT       300

CTTGT                                                                             305
```

( 2 ) INFORMATION FOR SEQ ID NO:14:

( i ) SEQUENCE CHARACTERISTICS:
        ( A ) LENGTH: 445 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Nicotiana tabacum
        ( C ) INDIVIDUAL ISOLATE: Ant68

( i x ) FEATURE:
        ( A ) NAME/KEY: CDS
        ( B ) LOCATION: 2..445

( x i ) SEQUENCE DESCRIPTION: SEQ ID NO:14:

```
A GTT  GGT  GGC  GGT  GGC  AGT  GGC  GGA  GGT  GGA  GCC  TAT  GGT  AGC  GGG         46
  Val  Gly  Gly  Gly  Gly  Ser  Gly  Gly  Gly  Gly  Ala  Tyr  Gly  Ser  Gly
  1                  5                        10                       15

TGT  GGT  GAA  AAT  GGC  TGT  AAT  TAC  CCG  CCC  GTT  GTA  CCT  GGA  CCT  CCA      94
Cys  Gly  Glu  Asn  Gly  Cys  Asn  Tyr  Pro  Pro  Val  Val  Pro  Gly  Pro  Pro
               20                       25                       30

CAA  ACA  GGC  GAA  AAC  CCT  TAT  TGC  ATG  CCT  GGT  TGT  GGC  GTA  GGT  GGT     142
Gln  Thr  Gly  Glu  Asn  Pro  Tyr  Cys  Met  Pro  Gly  Cys  Gly  Val  Gly  Gly
                35                       40                       45

GGT  GGG  GTA  GGC  GGC  AGT  AAT  GGC  GGA  AGT  GGC  GGT  GGA  GGA  GGC  GGT     190
Gly  Gly  Val  Gly  Gly  Ser  Asn  Gly  Gly  Ser  Gly  Gly  Gly  Gly  Gly  Gly
          50                       55                       60

GGT  GGT  GGC  GGA  GGT  GGA  GGT  GGA  GGA  TAT  GGT  AGT  GGT  TAT  GGT  GAA     238
Gly  Gly  Gly  Gly  Gly  Gly  Gly  Gly  Gly  Tyr  Gly  Ser  Gly  Tyr  Gly  Glu
```

|     |     |     |     | 65  |     |     |     |     | 70  |     |     |     |     | 75  |     |     |
|-----|-----|-----|-----|-----|-----|-----|-----|-----|-----|-----|-----|-----|-----|-----|-----|-----|
| AAT | GGA | AAT | TGT | AAT | TAC | CCA | CCC | GTT | ATA | CCT | GGA | CCC | CCA | CAA | ACA | 286 |
| Asn | Gly | Asn | Cys | Asn | Tyr | Pro | Pro | Val | Ile | Pro | Gly | Pro | Pro | Gln | Thr |     |
| 80  |     |     |     |     | 85  |     |     |     |     | 90  |     |     |     |     | 95  |     |
| ATT | GGA | CCT | ATA | TGC | AAT | TGT | CCA | ATA | ACT | CAA | CCA | ACA | TTC | CCA | TTT | 334 |
| Ile | Gly | Pro | Ile | Cys | Asn | Cys | Pro | Ile | Thr | Gln | Pro | Thr | Phe | Pro | Phe |     |
|     |     |     |     | 100 |     |     |     |     | 105 |     |     |     |     | 110 |     |     |
| CGT | TGT | CCA | TAT | GGA | TGT | CAG | CCA | CCA | CCT | AGT | TAT | GGC | TGC | CCA | AAT | 382 |
| Arg | Cys | Pro | Tyr | Gly | Cys | Gln | Pro | Pro | Pro | Ser | Tyr | Gly | Cys | Pro | Asn |     |
|     |     |     | 115 |     |     |     |     | 120 |     |     |     |     | 125 |     |     |     |
| GGA | AAT | TCC | AGA | CTA | ACT | CAT | GAC | AAG | GAA | AAA | CAG | AAT | CAT | CAG | CCC | 430 |
| Gly | Asn | Ser | Arg | Leu | Thr | His | Asp | Lys | Glu | Lys | Gln | Asn | His | Gln | Pro |     |
|     |     | 130 |     |     |     |     | 135 |     |     |     |     | 140 |     |     |     |     |
| AAG | ACT | ACT | GCT | TCG |     |     |     |     |     |     |     |     |     |     |     | 445 |
| Lys | Thr | Thr | Ala | Ser |     |     |     |     |     |     |     |     |     |     |     |     |
| 145 |     |     |     |     |     |     |     |     |     |     |     |     |     |     |     |     |

( 2 ) INFORMATION FOR SEQ ID NO:15:

( i ) SEQUENCE CHARACTERISTICS:
        ( A ) LENGTH: 148 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| Val | Gly | Gly | Gly | Gly | Ser | Gly | Gly | Gly | Gly | Ala | Tyr | Gly | Ser | Gly | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Glu | Asn | Gly | Cys | Asn | Tyr | Pro | Pro | Val | Val | Pro | Gly | Pro | Pro | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Gly | Glu | Asn | Pro | Tyr | Cys | Met | Pro | Gly | Cys | Gly | Val | Gly | Gly | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Val | Gly | Gly | Ser | Asn | Gly | Gly | Ser | Gly | Gly | Gly | Gly | Gly | Gly | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Gly | Gly | Gly | Gly | Gly | Gly | Gly | Tyr | Gly | Ser | Gly | Tyr | Gly | Glu | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Asn | Cys | Asn | Tyr | Pro | Pro | Val | Ile | Pro | Gly | Pro | Pro | Gln | Thr | Ile |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Pro | Ile | Cys | Asn | Cys | Pro | Ile | Thr | Gln | Pro | Thr | Phe | Pro | Phe | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Cys | Pro | Tyr | Gly | Cys | Gln | Pro | Pro | Pro | Ser | Tyr | Gly | Cys | Pro | Asn | Gly |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Asn | Ser | Arg | Leu | Thr | His | Asp | Lys | Glu | Lys | Gln | Asn | His | Gln | Pro | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Thr | Thr | Ala | Ser |
|-----|-----|-----|-----|
| 145 |     |     |     |

( 2 ) INFORMATION FOR SEQ ID NO:16:

( i ) SEQUENCE CHARACTERISTICS:
        ( A ) LENGTH: 3706 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO

-continued ( v i ) ORIGINAL SOURCE:
  ( A ) ORGANISM: Nicotiana tabacum
  ( C ) INDIVIDUAL ISOLATE: Ant32 genomic clone ( v i i ) IMMEDIATE SOURCE:
  ( B ) CLONE: pCIB950

( i x ) FEATURE:
  ( A ) NAME/KEY: TATA_signal
  ( B ) LOCATION: 1971..1975

( i x ) FEATURE:
  ( A ) NAME/KEY: CDS
  ( B ) LOCATION: 2076..3422

( i x ) FEATURE:
  ( A ) NAME/KEY: misc_feature
  ( B ) LOCATION: 2009
  ( D ) OTHER INFORMATION: /note="Putative transcription start site"

( x i ) SEQUENCE DESCRIPTION: SEQ ID NO:16:

```
CTGCAGTAAG GGGGATATTC AGAGACTCAA CTTAATCAAT ATTTGGCCCA AATTTGGCCT      60
GCCGCGTCAC CCAAGGCATC GCATCAGTGT AATTCTCTTC GCAATCTGAT TTTTGCTCTG     120
CTACCCTTCA TGAAAAAGT  CATAACTTCT TGTAGGAAAT ATTGGAATGA TAAATGGTTT     180
GATGTTCTGG AAACTAGACT CACAGAAAAT TCATTTGATA TATAGCTAAT AGCTCAATTC     240
GTAATGCATT CGGAGATATG ATTGTTTGAA GTTACATCAT ATGCGAGTAT GCTCGCTTTC     300
TTCTCTTAAA CCTTTTCTAT TTGTTCCAAA CTACTTCTTC TCACTTATAG ATGTCCATAT     360
AACTTTACAA ACATGAGATT TAGGTATTAC ACACCTTCAA AACTTTTCGA ACACACGTGT     420
GTCTACTTAG GGCTTGAACC AGAACGTAAT ACTTAACGAT TTTCGGGGCA TTACATGCAT     480
ACACCACTGT TAACAGGAAA ATTGCTTTCA TTAAATTATA ACATTGGATT TGGTGTGCAC     540
TAAGTTCCTA TGCTTAATTG TTATGAACAT GAGTACTTTG CTTTCTCCCT TTGGTGGTGC     600
ATACTTGTTT GTGGATATAT ATCGAGAATA ATAATGTGAG TGAATAGATA TTGTCTATTA     660
TTTAACTTTA ATTTGCACCG CTACTTGTTC ACCACATTGG GATTCAATTG GGTGACTCGG     720
CATATTTATC AATTAATATT CATCTAATGA GAACTCTTGC AAATTCTGTT ATAGGTTCTT     780
AGTAGCATCA GCTGCATATC ATGTAAACTA AGAGTCAATA TGCTCACTTG TCAGTAAAAA     840
AGAGTCATTA TCCTCACTTA TGTCATTTAC TCTATAGCTA TATTGGAGGC ATTATGTTAA     900
TGGATTCCTA ATAATACCAA ATTACACCTT ATATGAGTCA TTGTTGGACA GAGTTTATCA     960
ATACCTATAT ATTAGTGTAC TCTTATTCTT GCTCTTTGTG AGTATTAATA TGATGACTAT    1020
ATTGACAGCA TTTGCATGAT GATGAGTGGG GCAGGAGACG CACAAAGTTT GTACCATAGA    1080
GGAAGTTCGA GTTCTGTGAT AATCTTGGAA GAAAGTATAG TTATATTCTT TCTCCCCACC    1140
TTGTTGATTT CCGACTTGTT TGAAGTTTGC TCCTTGTTGC TGTCACAATT GTATTCATGT    1200
TAAGTTCTTT ATGAAGTTGG GTTGACGTTC AAATCTCATA CGCATGTTTG TTGCCTCTTT    1260
TTATTTGTCT ATGGGGGTTG CATCAGTTGT CTCAGATCAA GATGGGAGCA TATTACTGCT    1320
CCAAAGGTTT GGTTGTCCTT GGTAGTAACT AGTTCATGTG CAGGTTGGCT GCTCTGTTTG    1380
ATTCTGCTTT GAGAACTTAA AGCTTTCATT TACTCAATTA TCAAATATCT GGGGTTTAAT    1440
GGGCTCAAAT CACCCTTATA CAAACACCTT TTGTTTCCCT TATCAATGAA TGAACGAATT    1500
TCCTTTGAGT TGTGAATGTA ATAAGGGTGT GAAAGAGGAG TTTTCGTTGT TAAATTGGCG    1560
TTTGAAAGGT TCTCCCTTTT GTTCTTTTTT CGGCTTTTAC TTTTATATAC TGATAGTCTA    1620
AGAAACTTTT TACACTATCA AGTTGCCTAA AAGATAGCTA CATGAGTAAC TTGTTACAAC    1680
```

```
CGGTTAAATT ACACTAATAT TACAAATAAA AGTAAATCAG TAATATAAAA GTTATTTACA      1740

TAGTCAATAT ATATAATTTA AATCCTTTTC TATTTTTTCT CGAGGGGTTT GGATTTTTAT      1800

TTTAGTTGGC TCTTAAGACT TGTGCATGTA CATTCTTGAG AAAATAACTC TGTTCATGAG      1860

AAAGCTACCT TAACTAACTA ACGTACTTCA CGGCCGAAAC AAAATCATAC AAATAACACA      1920

TTTCTTTGTG GTTACCTTAA AATTTGGCCA TGAAACTTGG TCTGTTCGAT TATATCTTTA      1980

AATACTACTA CCATCTACCA CACACTCTCC TCTGTCAAGA TAACAATAAA AGAATAAAAA      2040

GATTAACCAA AAACGATATA CATATTTAGG ACAGA ATG AAG GTT AGC TTG AAG         2093
                                      Met Lys Val Ser Leu Lys
                                       1               5
```

| CAC | CAC | TGG | GTA | GTG | AAG | CCA | GCA | GAG | GCA | ACA | TGG | AAT | GGC | ACT | GTC | 2141 |
|---|---|---|---|---|---|---|---|---|---|---|---|---|---|---|---|---|
| His | His | Trp | Val | Val | Lys | Pro | Ala | Glu | Ala | Thr | Trp | Asn | Gly | Thr | Val | |
| | | | 10 | | | | | 15 | | | | | 20 | | | |

| TCC | TTA | TCG | GAG | TGT | GAT | CAA | ACT | TTT | GCT | GTA | ACT | CAT | GTA | CCA | ACC | 2189 |
|---|---|---|---|---|---|---|---|---|---|---|---|---|---|---|---|---|
| Ser | Leu | Ser | Glu | Cys | Asp | Gln | Thr | Phe | Ala | Val | Thr | His | Val | Pro | Thr | |
| | | 25 | | | | | 30 | | | | | 35 | | | | |

| ATT | TAT | TAC | TAC | AGG | TTT | TGC | CAT | GAT | TGT | CTT | CCA | TCA | ACA | GAC | AAT | 2237 |
|---|---|---|---|---|---|---|---|---|---|---|---|---|---|---|---|---|
| Ile | Tyr | Tyr | Tyr | Arg | Phe | Cys | His | Asp | Cys | Leu | Pro | Ser | Thr | Asp | Asn | |
| | 40 | | | | | 45 | | | | | 50 | | | | | |

| ATC | ATC | AAA | ACC | CTC | AGG | ACC | TCA | CTA | AGC | AAA | GCA | TTA | GTA | CAC | TTC | 2285 |
|---|---|---|---|---|---|---|---|---|---|---|---|---|---|---|---|---|
| Ile | Ile | Lys | Thr | Leu | Arg | Thr | Ser | Leu | Ser | Lys | Ala | Leu | Val | His | Phe | |
| 55 | | | | | 60 | | | | | 65 | | | | | 70 | |

| TAT | CCA | TTG | TCT | GGT | CGT | TTG | CGA | TGG | ATC | GCT | GGG | TCC | CGC | CTC | GAG | 2333 |
|---|---|---|---|---|---|---|---|---|---|---|---|---|---|---|---|---|
| Tyr | Pro | Leu | Ser | Gly | Arg | Leu | Arg | Trp | Ile | Ala | Gly | Ser | Arg | Leu | Glu | |
| | | | | 75 | | | | | 80 | | | | | 85 | | |

| CTC | GAC | TGT | AAT | GCC | TCG | GGA | ATC | GTG | CTC | ATG | GAA | GCT | GAA | ACC | GAA | 2381 |
|---|---|---|---|---|---|---|---|---|---|---|---|---|---|---|---|---|
| Leu | Asp | Cys | Asn | Ala | Ser | Gly | Ile | Val | Leu | Met | Glu | Ala | Glu | Thr | Glu | |
| | | | 90 | | | | | 95 | | | | | 100 | | | |

| GCC | AAA | CTA | GAT | GAT | CTT | GGC | GAT | TTC | TCG | CCA | TCC | CCT | GAC | TTG | AAC | 2429 |
|---|---|---|---|---|---|---|---|---|---|---|---|---|---|---|---|---|
| Ala | Lys | Leu | Asp | Asp | Leu | Gly | Asp | Phe | Ser | Pro | Ser | Pro | Asp | Leu | Asn | |
| | | 105 | | | | | 110 | | | | | 115 | | | | |

| AGC | TTG | TTT | CCC | CGT | GTA | GAC | TAC | ACA | ATC | CCA | ATT | GAT | GAA | CTC | CCT | 2477 |
|---|---|---|---|---|---|---|---|---|---|---|---|---|---|---|---|---|
| Ser | Leu | Phe | Pro | Arg | Val | Asp | Tyr | Thr | Ile | Pro | Ile | Asp | Glu | Leu | Pro | |
| | 120 | | | | | 125 | | | | | 130 | | | | | |

| TTG | TTG | TTT | GTT | CAG | CTT | ACT | AAG | TTT | CAG | TGT | GGT | GGT | ATT | GCT | CTG | 2525 |
|---|---|---|---|---|---|---|---|---|---|---|---|---|---|---|---|---|
| Leu | Leu | Phe | Val | Gln | Leu | Thr | Lys | Phe | Gln | Cys | Gly | Gly | Ile | Ala | Leu | |
| 135 | | | | | 140 | | | | | 145 | | | | | 150 | |

| AGT | TTT | GCA | ATA | TCA | CAT | GCT | GTA | GTT | GAT | GGC | CAA | AGT | GCT | CTT | TAC | 2573 |
|---|---|---|---|---|---|---|---|---|---|---|---|---|---|---|---|---|
| Ser | Phe | Ala | Ile | Ser | His | Ala | Val | Val | Asp | Gly | Gln | Ser | Ala | Leu | Tyr | |
| | | | | 155 | | | | | 160 | | | | | 165 | | |

| TTC | CTC | ACC | GAA | TGG | GCT | AGC | CTT | GCT | CGC | GGA | GAG | CCA | TTA | GGG | AAC | 2621 |
|---|---|---|---|---|---|---|---|---|---|---|---|---|---|---|---|---|
| Phe | Leu | Thr | Glu | Trp | Ala | Ser | Leu | Ala | Arg | Gly | Glu | Pro | Leu | Gly | Asn | |
| | | | 170 | | | | | 175 | | | | | 180 | | | |

| GAA | CCT | TTT | CAT | GAT | CGA | AAA | TTC | CTC | CGA | GCA | GGG | GAA | CCT | CCA | ATT | 2669 |
|---|---|---|---|---|---|---|---|---|---|---|---|---|---|---|---|---|
| Glu | Pro | Phe | His | Asp | Arg | Lys | Phe | Leu | Arg | Ala | Gly | Glu | Pro | Pro | Ile | |
| | | 185 | | | | | 190 | | | | | 195 | | | | |

| GCA | TAT | CCA | ACG | TTT | GAG | CAT | TTA | CAG | TTT | AAT | CCA | CCA | CCA | CTT | TTG | 2717 |
|---|---|---|---|---|---|---|---|---|---|---|---|---|---|---|---|---|
| Ala | Tyr | Pro | Thr | Phe | Glu | His | Leu | Gln | Phe | Asn | Pro | Pro | Pro | Leu | Leu | |
| | 200 | | | | | 205 | | | | | 210 | | | | | |

| CTT | GGA | CAG | TCC | AGC | AGT | GAA | GAG | GAG | AAG | AAA | AAT | GAA | ACA | AAG | GGT | 2765 |
|---|---|---|---|---|---|---|---|---|---|---|---|---|---|---|---|---|
| Leu | Gly | Gln | Ser | Ser | Ser | Glu | Glu | Glu | Lys | Lys | Asn | Glu | Thr | Lys | Gly | |
| 215 | | | | | 220 | | | | | 225 | | | | | 230 | |

| TCC | ATG | CTA | AAA | CTT | ACA | AAA | CAT | CAA | GTT | GAA | ATG | TTG | AGA | AAA | AAG | 2813 |
|---|---|---|---|---|---|---|---|---|---|---|---|---|---|---|---|---|
| Ser | Met | Leu | Lys | Leu | Thr | Lys | His | Gln | Val | Glu | Met | Leu | Arg | Lys | Lys | |
| | | | | 235 | | | | | 240 | | | | | 245 | | |

| GCG | AAC | CAA | GGT | AAT | CAA | GGG | CGT | AGT | TAC | ACA | CGT | TAT | GAA | GTT | GTG | 2861 |
|---|---|---|---|---|---|---|---|---|---|---|---|---|---|---|---|---|
| Ala | Asn | Gln | Gly | Asn | Gln | Gly | Arg | Ser | Tyr | Thr | Arg | Tyr | Glu | Val | Val | |
| | | | | 250 | | | | | 255 | | | | | 260 | | |

| | | | | | | | | | | | | | | | | |
|---|---|---|---|---|---|---|---|---|---|---|---|---|---|---|---|---|
| ACT | GCA | CAT | ATA | TGG | AGA | TGT | GCA | TGC | AAG | GCA | AGA | GGT | CAT | AAA | TTT | 2909 |
| Thr | Ala | His 265 | Ile | Trp | Arg | Cys | Ala 270 | Cys | Lys | Ala | Arg | Gly 275 | His | Lys | Phe | |
| GAG | CAG | CCT | ACT | AAT | TTA | TGC | ATT | TGT | GTT | AAC | ATA | CGC | AAT | ATA | ATG | 2957 |
| Glu | Gln | Pro 280 | Thr | Asn | Leu | Cys | Ile 285 | Cys | Val | Asn | Ile | Arg 290 | Asn | Ile | Met | |
| CAA | CCA | CCT | TTG | CCT | AAA | TCC | TAT | TTT | GGC | AAT | GCC | ATA | GTT | GAT | GTT | 3005 |
| Gln 295 | Pro | Pro | Leu | Pro | Lys | Ser 300 | Tyr | Phe | Gly | Asn | Ala 305 | Ile | Val | Asp | Val 310 | |
| ATT | GCC | AAT | GGC | GTC | TCG | GGT | GAC | ATT | ACC | TCG | AGG | CCA | TTG | GAG | TAT | 3053 |
| Ile | Ala | Asn | Gly | Val 315 | Ser | Gly | Asp | Ile | Thr 320 | Ser | Arg | Pro | Leu | Glu 325 | Tyr | |
| GTT | GCT | CGA | AGG | GTG | CGA | GCA | GCC | ATT | AAA | ATG | GTG | ACG | AGT | GAT | TAC | 3101 |
| Val | Ala | Arg | Arg 330 | Val | Arg | Ala | Ala | Ile 335 | Lys | Met | Val | Thr | Ser 340 | Asp | Tyr | |
| GCA | AAC | TCG | ACG | ATT | GAT | TTC | TTA | AAA | AAC | CAG | GAG | GAT | TTG | TCA | AAA | 3149 |
| Ala | Asn | Ser 345 | Thr | Ile | Asp | Phe | Leu 350 | Lys | Asn | Gln | Glu | Asp 355 | Leu | Ser | Lys | |
| TAT | CAA | GAT | ATT | CAT | GCA | TTT | AGA | AGC | AAG | GAA | GGT | CCT | TTT | TAT | GGA | 3197 |
| Tyr | Gln | Asp 360 | Ile | His | Ala | Phe | Arg 365 | Ser | Lys | Glu | Gly | Pro 370 | Phe | Tyr | Gly | |
| AAC | CCT | AAT | CTT | GGG | GTT | ATA | AGT | TGG | ATA | AGT | TTG | CCA | TTA | TTA | GGA | 3245 |
| Asn 375 | Pro | Asn | Leu | Gly | Val 380 | Ile | Ser | Trp | Ile | Ser 385 | Leu | Pro | Leu | Leu | Gly 390 | |
| TTG | GAT | TTT | GGG | TGG | GGA | AAA | GAG | ATA | CAT | ATG | AGC | CCT | GGA | ACT | CAT | 3293 |
| Leu | Asp | Phe | Gly | Trp 395 | Gly | Lys | Glu | Ile | His 400 | Met | Ser | Pro | Gly | Thr 405 | His | |
| GAA | TAT | GAT | GGT | GAT | TGT | GTG | ATA | CTT | CCA | GGA | AAA | GAA | GGG | GAT | GGA | 3341 |
| Glu | Tyr | Asp | Gly 410 | Asp | Cys | Val | Ile | Leu 415 | Pro | Gly | Lys | Glu | Gly 420 | Asp | Gly | |
| TCT | TTG | ACT | GTT | GCA | ATC | ATT | CTT | CAA | GCT | GTT | CAT | GTG | GAT | GCT | TTC | 3389 |
| Ser | Leu | Thr 425 | Val | Ala | Ile | Ile | Leu 430 | Gln | Ala | Val | His | Val 435 | Asp | Ala | Phe | |
| AAG | AAC | TTC | TTC | TAT | GAA | GAA | ATT | GAA | TGT | TGAAAAACAT | | AAGTGTTTTA | | | | 3439 |
| Lys | Asn 440 | Phe | Phe | Tyr | Glu | Glu 445 | Ile | Glu | Cys | | | | | | | |

```
TGAGAAGAAA  GGAAACAAAT  TAAGAACATG  TAGCTTTTCC  TAAATTGACA  TTGTTAGTCA    3499

TGGTCTAAGC  AAAATAAACT  CTTTATCTAC  ACATTATTTC  AATATATTTT  CCTTATTTTC    3559

TATCAGATTT  CTCATATGTT  TATTTGATGT  TCTTAATTTT  ACGACAATA   ATCGGTCATA    3619

AATGGTTTGA  AAATCAATAA  CCAAAACTGG  AACTATATTG  ATTGTTTGGA  AGCTAAGCAC    3679

TTTTTTTCTT  CTTTTTTCGC  AAAGCAC                                           3706
```

( 2 ) INFORMATION FOR SEQ ID NO:17:

( i ) SEQUENCE CHARACTERISTICS:
        ( A ) LENGTH: 448 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Met 1 | Lys | Val | Ser | Leu 5 | Lys | His | His | Trp | Val 10 | Val | Lys | Pro | Ala | Glu 15 | Ala |
| Thr | Trp | Asn | Gly 20 | Thr | Val | Ser | Leu | Ser 25 | Glu | Cys | Asp | Gln | Thr 30 | Phe | Ala |
| Val | Thr | His 35 | Val | Pro | Thr | Ile | Tyr 40 | Tyr | Tyr | Arg | Phe | Cys 45 | His | Asp | Cys |

| | | | | | | | | | | | | | | |
|---|---|---|---|---|---|---|---|---|---|---|---|---|---|---|
| Leu | Pro | Ser | Thr | Asp | Asn | Ile | Ile | Lys | Thr | Leu | Arg | Thr | Ser | Leu | Ser |
| | 50 | | | | 55 | | | | | 60 | | | | |
| Lys | Ala | Leu | Val | His | Phe | Tyr | Pro | Leu | Ser | Gly | Arg | Leu | Arg | Trp | Ile |
| 65 | | | | 70 | | | | | 75 | | | | | 80 | |
| Ala | Gly | Ser | Arg | Leu | Glu | Leu | Asp | Cys | Asn | Ala | Ser | Gly | Ile | Val | Leu |
| | | | | 85 | | | | | 90 | | | | | 95 | |
| Met | Glu | Ala | Glu | Thr | Glu | Ala | Lys | Leu | Asp | Asp | Leu | Gly | Asp | Phe | Ser |
| | | | 100 | | | | | 105 | | | | 110 | | | |
| Pro | Ser | Pro | Asp | Leu | Asn | Ser | Leu | Phe | Pro | Arg | Val | Asp | Tyr | Thr | Ile |
| | | 115 | | | | | 120 | | | | | 125 | | | |
| Pro | Ile | Asp | Glu | Leu | Pro | Leu | Leu | Phe | Val | Gln | Leu | Thr | Lys | Phe | Gln |
| | 130 | | | | | 135 | | | | | 140 | | | | |
| Cys | Gly | Gly | Ile | Ala | Leu | Ser | Phe | Ala | Ile | Ser | His | Ala | Val | Val | Asp |
| 145 | | | | | 150 | | | | | 155 | | | | | 160 |
| Gly | Gln | Ser | Ala | Leu | Tyr | Phe | Leu | Thr | Glu | Trp | Ala | Ser | Leu | Ala | Arg |
| | | | | 165 | | | | | 170 | | | | | 175 | |
| Gly | Glu | Pro | Leu | Gly | Asn | Glu | Pro | Phe | His | Asp | Arg | Lys | Phe | Leu | Arg |
| | | | 180 | | | | | 185 | | | | | 190 | | |
| Ala | Gly | Glu | Pro | Pro | Ile | Ala | Tyr | Pro | Thr | Phe | Glu | His | Leu | Gln | Phe |
| | | | 195 | | | | 200 | | | | | 205 | | | |
| Asn | Pro | Pro | Pro | Leu | Leu | Leu | Gly | Gln | Ser | Ser | Ser | Glu | Glu | Glu | Lys |
| | 210 | | | | | 215 | | | | | 220 | | | | |
| Lys | Asn | Glu | Thr | Lys | Gly | Ser | Met | Leu | Lys | Leu | Thr | Lys | His | Gln | Val |
| 225 | | | | | 230 | | | | | 235 | | | | | 240 |
| Glu | Met | Leu | Arg | Lys | Lys | Ala | Asn | Gln | Gly | Asn | Gln | Gly | Arg | Ser | Tyr |
| | | | | 245 | | | | | 250 | | | | | 255 | |
| Thr | Arg | Tyr | Glu | Val | Val | Thr | Ala | His | Ile | Trp | Arg | Cys | Ala | Cys | Lys |
| | | | 260 | | | | | 265 | | | | | 270 | | |
| Ala | Arg | Gly | His | Lys | Phe | Glu | Gln | Pro | Thr | Asn | Leu | Cys | Ile | Cys | Val |
| | | 275 | | | | | 280 | | | | | 285 | | | |
| Asn | Ile | Arg | Asn | Ile | Met | Gln | Pro | Pro | Leu | Pro | Lys | Ser | Tyr | Phe | Gly |
| | 290 | | | | | 295 | | | | | 300 | | | | |
| Asn | Ala | Ile | Val | Asp | Val | Ile | Ala | Asn | Gly | Val | Ser | Gly | Asp | Ile | Thr |
| 305 | | | | | 310 | | | | | 315 | | | | | 320 |
| Ser | Arg | Pro | Leu | Glu | Tyr | Val | Ala | Arg | Arg | Val | Arg | Ala | Ala | Ile | Lys |
| | | | | 325 | | | | | 330 | | | | | 335 | |
| Met | Val | Thr | Ser | Asp | Tyr | Ala | Asn | Ser | Thr | Ile | Asp | Phe | Leu | Lys | Asn |
| | | | 340 | | | | | 345 | | | | 350 | | | |
| Gln | Glu | Asp | Leu | Ser | Lys | Tyr | Gln | Asp | Ile | His | Ala | Phe | Arg | Ser | Lys |
| | | 355 | | | | | 360 | | | | | 365 | | | |
| Glu | Gly | Pro | Phe | Tyr | Gly | Asn | Pro | Asn | Leu | Gly | Val | Ile | Ser | Trp | Ile |
| | 370 | | | | | 375 | | | | | 380 | | | | |
| Ser | Leu | Pro | Leu | Leu | Gly | Leu | Asp | Phe | Gly | Trp | Gly | Lys | Glu | Ile | His |
| 385 | | | | | 390 | | | | | 395 | | | | | 400 |
| Met | Ser | Pro | Gly | Thr | His | Glu | Tyr | Asp | Gly | Asp | Cys | Val | Ile | Leu | Pro |
| | | | | 405 | | | | | 410 | | | | | 415 | |
| Gly | Lys | Glu | Gly | Asp | Gly | Ser | Leu | Thr | Val | Ala | Ile | Ile | Leu | Gln | Ala |
| | | | 420 | | | | | 425 | | | | | 430 | | |
| Val | His | Val | Asp | Ala | Phe | Lys | Asn | Phe | Phe | Tyr | Glu | Glu | Ile | Glu | Cys |
| | | | 435 | | | | | 440 | | | | | 445 | | |

( 2 ) INFORMATION FOR SEQ ID NO:18:

( i ) SEQUENCE CHARACTERISTICS:
    ( A ) LENGTH: 1906 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Nicotiana tabacum
    ( C ) INDIVIDUAL ISOLATE: Ant43D ( v i i ) IMMEDIATE SOURCE:
    ( B ) CLONE: pCIB952

( i x ) FEATURE:
    ( A ) NAME/KEY: CDS
    ( B ) LOCATION: join(1230..1570, 1669..1684)

( i x ) FEATURE:
    ( A ) NAME/KEY: intron
    ( B ) LOCATION: 1571..1668

( i x ) FEATURE:
    ( A ) NAME/KEY: misc_feature
    ( B ) LOCATION: 1167
    ( D ) OTHER INFORMATION: /note="Putative transcriptional start site"

( x i ) SEQUENCE DESCRIPTION: SEQ ID NO:18:

```
GAATTCCTCG ATTTAACCAG AAATCTGCAA AAAATCCCTC AATTCAGCTA ATTAGGACTC      60
TGATACCATG TTAACTTTCA CTGATTTATA CTGATTATGA AGTGTAATCC ACAACTGAAT     120
GAATTGAGAA GACGAAATTG AAAGCAGAAG AAAGGTAAAG AACAGAGAGA ACAATATGAT     180
TACTTCTCTG CTTAGCAATG TCGGTCATTA CTAACAAAAT GAATGTATAC ATATACTTAT     240
ACTAATATTT ATTGACTCCT AATAGATGAC CGTTGTAAAT AAGAAAAATG ACATAATTAC     300
TCCTGTAGCT AACTAATGAT CAGGGAATTA TAGTGCAATT AACTAACTCC TTTACAAAAC     360
CCGATTTACT TTGATGCGAT TGACTTTTTC ATATATCTTA ATTAATGGA AAGAATCTGT      420
GATTATCACA CCTTATTTAG AGAAGATCTT TTAAAAGTAA GGAGGCATCG CCTAAAACAT     480
CTTAATAACT TCCTTTTCAC CGCATAAAAT AAGTGTGTAA ACCGTAGTAG TGTGTAAACC     540
AGCAAAAGAA CAACCATATA AAGAAAAATA TGTGAAATTA TATTTAAGCC GCTCCCAAAA     600
ATAATAGCCG ATAAAATGTA TATTTTTCAT ACATTATGTG TATGTATTAT ATACGAAAAA     660
GATACATATT TTATATACTT TTTGACAAAT GAATACAATT AGTTTCGGTC AACCTGCCAA     720
TTTTATATTT TGCCCTAAAA ATATACCCAA CAAAAGAGA CTTGTATGT AAAAAAAAAA       780
AAAAAATTAC TATGTGCAAA GTTAAGATCG GCAGGCTGCC TTAAAATCCC AAAAAAAAAA     840
AAAAAAAAAA AAATGGCTTG CTTTAATTAC ACATGAACAG CCAATGGTTT GCTTTAATTT     900
ATTCCTCTAA TACGTATATT GTCGTTGACA GAGAATTTGA ATCAAGCAAC TCACATCTCC     960
AAATAGAAGA GGAAATATCG TGTGAAATTC CAATTGAACA ACAAACTGCG CAGAGAATTG    1020
AAAACTCTAA TTCATGAGAA TCGCATGTTA CAAGTTACTA TAACAGAATA AAGGGGCTGA    1080
AAGATAGGTA TATATATATA TATATATATA TATATATATA TATATATATA TATATATATA    1140
TATATATGTC ACTCATTTGC ACATAATTCT ACACACAGAG AGAATTTAAC TTACATTTCT    1200
TCAATAGTTT AGTCCATAAA GCAATAGAT ATG GCT CGG TTT CTT GTG TTC CTT     1253
                                Met Ala Arg Phe Leu Val Phe Leu
                                 1               5
```

```
GCT  TTA  GCC  CTT  GTA  ATA  ATT  TCA  AAG  AAG  GGC  GCG  TTG  GGT  GCT  CCT     1301
Ala  Leu  Ala  Leu  Val  Ile  Ile  Ser  Lys  Lys  Gly  Ala  Leu  Gly  Ala  Pro
     10                       15                      20

CCT  TCC  TGT  CCA  ACA  GTT  ACA  ACG  CAG  CTG  GCT  CCT  TGT  CTA  TCG  TAC     1349
Pro  Ser  Cys  Pro  Thr  Val  Thr  Thr  Gln  Leu  Ala  Pro  Cys  Leu  Ser  Tyr
25                       30                      35                           40

ATT  CAA  GGT  GGA  GGT  GAT  CCA  TCT  GTA  CCT  TGC  TGC  ACT  GGT  ATA  AAT     1397
Ile  Gln  Gly  Gly  Gly  Asp  Pro  Ser  Val  Pro  Cys  Cys  Thr  Gly  Ile  Asn
                    45                      50                      55

AAC  ATA  TAT  GAA  CTT  GCT  AAA  ACC  AAA  GAA  GAC  CGA  GTC  GCT  ATC  TGC     1445
Asn  Ile  Tyr  Glu  Leu  Ala  Lys  Thr  Lys  Glu  Asp  Arg  Val  Ala  Ile  Cys
               60                      65                      70

AAC  TGC  TTA  AAA  ACC  GCA  TTT  ACT  CAT  GCT  GGA  AAT  GTC  AAT  CCC  ACT     1493
Asn  Cys  Leu  Lys  Thr  Ala  Phe  Thr  His  Ala  Gly  Asn  Val  Asn  Pro  Thr
          75                      80                      85

CTC  GTA  GCT  CAA  CTC  CCC  AAG  AAA  TGT  GGC  ATT  TCT  TTT  AAT  ATG  CCT     1541
Leu  Val  Ala  Gln  Leu  Pro  Lys  Lys  Cys  Gly  Ile  Ser  Phe  Asn  Met  Pro
     90                       95                      100

CCT  ATT  GAT  AAA  AAC  TAC  GAC  TGT  AAC    AC   GTAAGTTTAT ATTACCTCTC          1590
Pro  Ile  Asp  Lys  Asn  Tyr  Asp  Cys  Asn    Thr
105                      110

AATTTTTATT  TCCACCCAAT  TTGGTGCAGA  TCGACTGCTT  GTTTAATCTA  ACTTATTATT            1650

TTTATTACAT  GCATGCAG G  ATT  TCT  ATG  TAC  TGATGAATGG  GTAGTGAATC                1701
                       Ile  Ser  Met  Tyr
                       115

TCGGAAGCTG  CTCAAATTTA  TGAATAAAAC  ATATATAGAT  GTTCATCTCA  TGTCTGAAAT            1761

CTGAAAGCAA  TTTGATCCAC  TGTAAACTTC  AAATGTATGC  AGACGGTAAA  ATGTTGAATT            1821

ATGATATATA  TAAATTTGGT  TAATGCCTTT  GTTTTGGTA   GTCTTAGACC  AAGTTCACCA            1881

AGAGAGACGG  TTCATATGAG  CTTTT                                                    1906
```

( 2 ) INFORMATION FOR SEQ ID NO:19:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Ala  Arg  Phe  Leu  Val  Phe  Leu  Ala  Leu  Ala  Leu  Val  Ile  Ile  Ser
1                 5                        10                      15

Lys  Lys  Gly  Ala  Leu  Gly  Ala  Pro  Pro  Ser  Cys  Pro  Thr  Val  Thr  Thr
               20                       25                      30

Gln  Leu  Ala  Pro  Cys  Leu  Ser  Tyr  Ile  Gln  Gly  Gly  Gly  Asp  Pro  Ser
          35                      40                      45

Val  Pro  Cys  Cys  Thr  Gly  Ile  Asn  Asn  Ile  Tyr  Glu  Leu  Ala  Lys  Thr
     50                      55                      60

Lys  Glu  Asp  Arg  Val  Ala  Ile  Cys  Asn  Cys  Leu  Lys  Thr  Ala  Phe  Thr
65                       70                      75                          80

His  Ala  Gly  Asn  Val  Asn  Pro  Thr  Leu  Val  Ala  Gln  Leu  Pro  Lys  Lys
                    85                      90                      95

Cys  Gly  Ile  Ser  Phe  Asn  Met  Pro  Pro  Ile  Asp  Lys  Asn  Tyr  Asp  Cys
               100                     105                     110

Asn  Thr  Ile  Ser  Met  Tyr
          115
```

( 2 ) INFORMATION FOR SEQ ID NO:20:

( i ) SEQUENCE CHARACTERISTICS:
        ( A ) LENGTH: 437 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Nicotiana tabacum
        ( C ) INDIVIDUAL ISOLATE: Ant43C ( i x ) FEATURE:
        ( A ) NAME/KEY: CDS
        ( B ) LOCATION: 167..436

( x i ) SEQUENCE DESCRIPTION: SEQ ID NO:20:

```
CTGTGATTAA GGATACTGTC ACCCCTGTGA ATTTGGTTGG ATATGGGTTG GCTTTCTTGG      60

GTGACAGTAT CCTTAATCAC AGACCAAGAA AAGGCAATCA ACAACCAATC CTACACACAC    120

ACATTTAAAT TACATTTCTT CAATTGTAGT CCATAAACCA ATAGAT ATG GCT CGG       175
                                                Met Ala Arg
                                                  1

TTT CTT GCT TTA GCC CTA GTA GTT ATA GCT CTC TCA AAC GAC GCG TTG      223
Phe Leu Ala Leu Ala Leu Val Val Ile Ala Leu Ser Asn Asp Ala Leu
      5               10                  15

GGT GCT CCT CCC TCG TGT CAA ACT GTT ACA ACG CAG CTG GCT CCT TGT      271
Gly Ala Pro Pro Ser Cys Gln Thr Val Thr Thr Gln Leu Ala Pro Cys
 20              25                  30                      35

CTA TCG TAC ATT CAA AAT CGT GTT AAG GGC GGT GGC AAT CCA TCA GTA      319
Leu Ser Tyr Ile Gln Asn Arg Val Lys Gly Gly Gly Asn Pro Ser Val
                 40                  45                  50

CCT TGT TGT ACC GGT ATA AAT AAC ATA TAT GAA CTC GCT AAA ACC AAA      367
Pro Cys Cys Thr Gly Ile Asn Asn Ile Tyr Glu Leu Ala Lys Thr Lys
             55                  60                  65

GAA GAT CGA GTC GCT ATC TGC AAC TGC TTA AAA AAC GCA TTT ATT CAT      415
Glu Asp Arg Val Ala Ile Cys Asn Cys Leu Lys Asn Ala Phe Ile His
         70                  75                  80

GCT GGA AAT GTC AAT CCC ACC C                                        437
Ala Gly Asn Val Asn Pro Thr
     85              90
```

( 2 ) INFORMATION FOR SEQ ID NO:21:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met Ala Arg Phe Leu Ala Leu Ala Leu Val Val Ile Ala Leu Ser Asn
 1               5                  10                  15

Asp Ala Leu Gly Ala Pro Pro Ser Cys Gln Thr Val Thr Thr Gln Leu
             20                  25                  30

Ala Pro Cys Leu Ser Tyr Ile Gln Asn Arg Val Lys Gly Gly Gly Asn
         35                  40                  45

Pro Ser Val Pro Cys Cys Thr Gly Ile Asn Asn Ile Tyr Glu Leu Ala
     50                  55                  60
```

-continued

```
Lys Thr Lys Glu Asp Arg Val Ala Ile Cys Asn Cys Leu Lys Asn Ala
 65              70              75              80
Phe Ile His Ala Gly Asn Val Asn Pro Thr
             85              90
```

TABLE 1

Developmental Expression Profile of Anther cDNAs

|        | Bud Length in mm | | | | | | cDNA size | mRNA size | genomic Southern # Hind III bands |
|--------|------|-------|-------|-------|-------|-------|-----------|-----------|-----------------|
|        | 10–15 | 15–20 | 20–25 | 25–30 | 30–40 | 40–50 |           |           |                 |
| ant5   | +    | +     | +     | +     |       |       | .9 kb     | 1.8kb     | 6               |
| ant9   | +    | +     |       |       |       |       | .6        | 1.0       | 9               |
| ant32  | +    | +     |       |       |       |       | 1.5       | 1.9       | 2               |
| ant43C | +    | +     |       |       |       |       | .43       | 1.0       | 2               |
| ant43D | +    | +     | +     | +     | +     | +     | .55       | 1.0       | 2               |
| ant45  | +    | +     | +     | +     |       |       | .8        | 1.8       | 6               |
| ant52  | +    | +     | +     | +     | +     | +     | .1        | 1.0       | 4               |
| ant59  | +    | +     | +     |       |       |       | 1.2       | 1.9       | 2               |
| ant66  |      |       |       |       | +     | +     | .95       | 3.5       | 2               |
| ant67  | +    | +     | +     | +     | +     | +     | .3        | 1.4       | 2               |
| ant68  | +    | +     |       |       |       |       | .45       | 1.3       | >8              |

What is claimed is:

1. An isolated nucleotide sequence consisting of an anther-specific genomic DNA sequence selected from the group consisting of the sequences of SEQ. ID No. 16 and SEQ. ID No. 18.

2. A DNA sequence comprising, in a 5' to 3' direction, an anther promoter region from an anther-specific genomic DNA sequence of claim 1 operatively linked to a heterologous coding DNA sequence.

3. A DNA sequence comprising, in a 5' to 3' direction, an anther promoter region from an anther-specific genomic DNA sequence of claim 1, operatively linked to a signal sequence, which is operatively linked to a heterologous coding DNA sequence.

4. The DNA sequence according to claim 2, wherein the coding DNA sequence encodes a polypeptide which will disrupt formation of viable pollen when expressed in the anther cells.

5. The DNA sequence according to claim 4, wherein the coding DNA sequence encodes a polypeptide selected from the group consisting of DTA, TURF-13, pectate lyase, gin recombinase, iaaL and cytA toxin.

6. A plasmid selected from the group consisting of pCIB3132 and pCIB3178.

7. An anther-specific promoter fragment derived from the plasmid of claim 6.

8. An isolated recombinant DNA sequence comprising, in a 5' to 3' direction, the promoter fragment of claim 7 operably linked to a heterologous coding DNA sequence.

9. A DNA sequence comprising, in a 5' to 3' direction, the promoter fragment of claim 7, operably linked to a signal sequence, which is operably linked to a heterologous coding DNA sequence.

10. A transgenic plant which has been transformed with the DNA sequence of claim 2.

11. A transgenic plant which has been transformed with the DNA sequence of claim 3.

12. A transgenic plant which has been transformed with the DNA sequence of claim 4.

13. A transgenic plant which has been transformed with the DNA sequence of claim 5.

14. A transgenic plant which has been transformed with the DNA sequence of claim 8.

15. A transgenic plant which has been transformed with the DNA sequence of claim 9.

* * * * *